US011567073B2

(12) United States Patent
Martin-Fernandez et al.

(10) Patent No.: US 11,567,073 B2
(45) Date of Patent: Jan. 31, 2023

(54) RECEPTOR TYROSINE KINASE BIOMARKERS

(71) Applicant: The Science and Technology Facilities Council, Chilton (GB)

(72) Inventors: Marisa Martin-Fernandez, Hinton Waldrist (GB); David Clarke, Hinton Waldrist (GB); Sarah Needham, Wantage (GB); Daniel Rolfe, Wantage (GB); Michael Hirsch, Oxford (GB)

(73) Assignee: United Kingdom Research and Innovation, Swindon (GB)

( * ) Notice: Subject to any disclaimer, the term of this patent is extended or adjusted under 35 U.S.C. 154(b) by 819 days.

(21) Appl. No.: 15/569,871

(22) PCT Filed: Apr. 28, 2016

(86) PCT No.: PCT/GB2016/051200
§ 371 (c)(1),
(2) Date: Apr. 23, 2018

(87) PCT Pub. No.: WO2016/174434
PCT Pub. Date: Nov. 3, 2016

(65) Prior Publication Data
US 2018/0120313 A1    May 3, 2018

(30) Foreign Application Priority Data

Apr. 28, 2015 (GB) .................................. 1507202

(51) Int. Cl.
*A61K 39/395* (2006.01)
*G01N 33/566* (2006.01)
*G01N 33/58* (2006.01)
*A61P 35/00* (2006.01)
*C12N 9/12* (2006.01)

(52) U.S. Cl.
CPC .... *G01N 33/566* (2013.01); *C12Y 207/10001* (2013.01); *G01N 33/582* (2013.01); *A61P 35/00* (2018.01); *C12N 9/12* (2013.01); *G01N 2800/52* (2013.01)

(58) Field of Classification Search
None
See application file for complete search history.

(56) References Cited

U.S. PATENT DOCUMENTS 8,323,883 B1    12/2012  Sordella et al.

FOREIGN PATENT DOCUMENTS

| CN | 101672779 A | 3/2010 |
| CN | 103626871 A | 3/2014 |
| EP | 2169387 A2 | 3/2010 |
| WO | WO 2007/039705 A1 | 4/2007 |

OTHER PUBLICATIONS

International Search Report and Written Opinion dated Sep. 26, 2016 in connection with Application No. PCT/GB2016/051200.
International Preliminary Report on Patentability dated Oct. 31, 2017 in connection with Application No. PCT/GB2016/051200.
Arora et al., Role of tyrosine kinase inhibitors in cancer therapy. J Pharmacol Exp Ther. Dec. 2005;315(3):971-9. Epub Jul. 7, 2005. Review.
Arteaga et al., Treatment of HER2-positive breast cancer: current status and future perspectives. Nat Rev Clin Oncol. Nov. 29, 2011;9(1): 16-32. doi: 10.1038/nrclinonc.2011.177. Review.
Coban et al., Effect of phosphorylation on EGFR dimer stability probed by single-molecule dynamics and FRET/FLIM. Biophys J. Mar. 10, 2015;108(5):1013-26. doi: 10.1016/j.bpj.2015.01.005.
Dziadziuszko et al., Selecting lung cancer patients for treatment with epidermal growth factor receptor tyrosine kinase inhibitors by immunohistochemistry and fluorescence in situ hybridization—why, when, and how? Clin Cancer Res. Jul. 15, 2006;12(14 Pt 2):4409s-4415s. doi: 10.1158/1078-0432.CCR-06-0087.
Han et al., Predictive and prognostic impact of epidermal growth factor receptor mutation in non-small-cell lung cancer patients treated with gefitinib. J Clin Oncol. Apr. 10, 2005;23(11):2493-501. doi: 10.1200/JCO.2005.01.388. Epub Feb. 14, 2005.
Ibach, Single molecule imaging of the signaling activity of the epidermal growth factor receptor. Dissertation. Jan. 2014; 108 pages. Retrieved from the Internet: https://eldorado.tu-dortmund.de/bitstream/2003/32884/1/Dissertation.pdf [retrieved on Jun. 24, 2016] 108 pages.
Lee et al., Epidermal growth factor receptor activation in glioblastoma through novel missense mutations in the extracellular domain. PLoS Med. Dec. 2006;3(12):e485.
Mok, Personalized medicine in lung cancer: what we need to know. Nat Rev Clin Oncol. Aug. 23, 2011;8(11):661-8. doi: 10.1038/nrclinonc.2011.126. Review.
Needham et al., Measuring EGFR separations on cells with ~ 10 nm resolution via fluorophore localization imaging with photobleaching. PLoS One. May 1, 2013;8(5):e62331. doi: 10.1371/journal.pone.0062331.
Needham et al., Structure-function relationships and supramolecular organization of the EGFR (epidermal growth factor receptor) on the cell surface. Biochem Soc Trans. Feb. 2014;42(1):114-9. doi: 10.1042/BST20130236.
Takeuchi et al., Receptor tyrosine kinases and targeted cancer therapeutics. Biol Pharm Bull. 2011;34(12):1774-80. Review. Ullrich et al., Human epidermal growth factor receptor cDNA sequence and aberrant expression of the amplified gene in A431 epidermoid carcinoma cells. Nature. May 31-Jun. 6, 1984;309(5967):418-25.

(Continued)

*Primary Examiner* — Michael D Pak
(74) *Attorney, Agent, or Firm* — Wolf, Greenfield & Sacks, P.C.

(57) ABSTRACT

The present invention relates to the use of receptor tyrosine kinase (RTK) oligomers as markers of RTK activation and signalling. Methods are described based upon determining the presence of RTK oligomers and/or determining the nanometre spatial separation between RTK molecules assembled as RTK oligomers at the cell surface. Such methods are directed to the monitoring of RTK activation in cells and the detection of mutations in RTKs. Methods are also described for determining prognosis for subjects having diseases characterised by aberrant RTK activation and for selecting subjects for treatment with RTK inhibitors.

18 Claims, 7 Drawing Sheets

(56) References Cited

OTHER PUBLICATIONS

Zanetti-Domingues et al., Determining the geometry of oligomers of the human epidermal growth factor family on cells with 7 nm resolution. Prog Biophys Mol Biol. Sep. 2015;118(3):139-52. doi: 10.1016/j.pbiomolbio.2015.04.002. Epub Apr. 18, 2015.
PCT/GB2016/051200, Sep. 26, 2016, International Search Report and Written Opinion.
PCT/GB2016/051200, Oct. 31, 2017, International Preliminary Report on Patentability.
Yarden, The EGFR family and its ligands in human cancer, signalling mechanisms and therapeutic opportunities. Eur J Cancer. Sep. 2001;37 Suppl 4:S3-8. doi: 10.1016/s0959-8049(01)00230-1.

RECEPTOR TYROSINE KINASE BIOMARKERS

FIELD OF THE INVENTION

The present invention relates to the use of receptor tyrosine kinase (RTK) oligomers as markers of RTK activation and signalling. Methods are described based upon determining the presence of RTK oligomers and/or determining the nanometre spatial separation between RTK molecules assembled as RTK oligomers at the cell surface. Such methods are directed to the monitoring of RTK activation in cells and the detection of mutations in RTKs. Methods are also described for determining prognosis for subjects having diseases characterised by aberrant RTK activation and for selecting subjects for treatment with RTK inhibitors.

BACKGROUND TO THE INVENTION

Receptor tyrosine kinases (RTKs) are a family of integral cell surface receptor proteins having intrinsic tyrosine kinase activity (Lemmon and Schlessinger, Cell. 2010 Jun. 25; 141(7):1117-34). There are approximately 60 RTKs found in humans and although significant diversity exists between different members of the family, there is a basic architecture common to all RTKs. In particular, all RTKs possess an extracellular region allowing for ligand binding, a single transmembrane helix and an intracellular or cytoplasmic domain, a portion of which possesses the intrinsic tyrosine kinase activity.

RTKs are involved in the transmission of signals from the outside of cells to intracellular compartments, and play a key role in regulating fundamental physiological and cellular processes such as development, proliferation, differentiation, cell survival, metabolism, cell migration, cell cycle control, and wound healing. RTKs typically exist in the cell membrane in an inactive state and become activated upon ligand binding to their extracellular region. Different RTKs are responsive to different ligands but in all cases, ligand binding results in receptor dimerisation, i.e. the association of two receptor subunits as a complex, and/or receptor activation.

The precise means by which ligand binding brings about dimerisation and/or receptor activation varies between different members of the RTK family. However, activation of all RTKs is characterised by a stimulation of the intrinsic tyrosine kinase activity present in the intracellular or cytoplasmic region of the receptor. Activation is also accompanied by autophosphorylation of tyrosine residues in the intracellular region of the receptor. This phosphorylation typically triggers activation of one or more intracellular signalling pathways that serve to relay information from the cell membrane to the nucleus and other intracellular cell compartments.

Almost certainly as a result of the fundamental role played by RTKs in controlling processes such as cell proliferation and differentiation, dysregulated RTK signalling has been linked to the development of a variety of diseases and disorders. These diseases include cancer, diabetes, atherosclerosis, bone disorders and inflammatory disorders. Aberrant RTK signalling has been associated with the development of numerous cancers and several tyrosine kinase inhibitors have been developed and approved for use in the clinic as anti-cancer agents (Takeuchi et al. Biol Pharm Bull. 2011; 34(12): 1774-80 and Arora et al. J Pharmacol Exp Ther. 2005 December; 315(3): 971-9). Researchers continue to study RTKs as key therapeutic targets in cancer with recent efforts focussed on understanding how resistance to tyrosine kinase inhibitors develops in some cancer patients.

The Epidermal Growth Factor Receptor or "EGFR" was one of the first RTKs to be identified and the gene was cloned in 1984 (Ullrich et al. Nature 1984 May 31-Jun. 6; 309 (5967): 418-25). The EGFR is often considered the "prototypical" RTK and plays a fundamental role in the regulation of several key cellular processes including cell growth, metabolism and differentiation. The EGFR is one of a subfamily of four RTKs in humans known as the EGFR or ErbB family. The other three receptors in this family are ErbB2/HER2, ErbB3/HER3 and ErbB4/HER4.

Dysregulation of signalling via the EGFR family of receptors has been linked to the development and progression of a number of cancers including lung cancer (Mok TS Nat Rev Clin Oncol. 2011 Aug. 23; 8(11): 661-8), breast cancer (Arteaga et al. Nat Rev Clin Oncol. 2011 Nov. 29; 9(1): 16-32) and glioblastoma (Lee et al. PLoS Med. 2006 December; 3(12)). Receptor overexpression and/or mutations in the receptor have been identified that correlate with elevated signalling, constitutive activation and/or ligand-independent signalling via EGFR in cancer cells. Given the importance of dysregulated EGFR signalling in cancer, a number of anticancer drugs have been developed to target members of this family including the antibody Trastuzumab (Herceptin), which targets the HER2 receptor, and the small molecule drugs Gefitinib (Iressa) and Erlotinib (Tarceva), which target the EGFR.

In recent years, structural studies have shed light on the precise mechanisms by which receptor dimerisation leads to activation of receptors of the EGFR family. More recently, a new high-resolution imaging technique has been developed allowing for the detailed study of EGFR organisation at the cell membrane (Needham et al. PLoS One. 2013 May 1; 8(5)). This imaging technique, referred to as Fluorophore Localisation Imaging with Photobleaching or "FLImP", has revealed the clustering of EGFR molecules into oligomers i.e. clusters of associated receptors consisting of more than two receptor molecules. The presence of these EGFR higher-order oligomers at the surface of cells has been observed previously. However, the precise architecture and role of these oligomeric structures in RTK activation and downstream signalling is unknown.

SUMMARY OF INVENTION

The present inventors have identified for the first time, an essential role for RTK oligomers in RTK phosphorylation and activation. It has also been found that the organisation of these RTK oligomers and in particular, the nanometre spatial separation between RTK molecules in such oligomers, relates to the signalling properties of the RTK. The present invention is thus drawn to methods based on use of RTK oligomers as structural biomarkers predictive of RTK activation.

In a first aspect, the present invention provides a method of monitoring receptor tyrosine kinase (RTK) activation in a cell, the method comprising the steps of:
  (i) imaging RTK molecules at the cell surface; and
  (ii) determining the presence of one or more RTK oligomers wherein the RTK oligomers comprise more than two RTK monomers,
wherein the one or more RTK oligomers is/are indicative of RTK activation in said cell.

The inventors have observed a particular link between the nanometre spatial separation of RTK molecules assembled as RTK oligomers at the cell surface and the presence of mutations in the RTK, particularly in the intracellular region. Thus, in a second aspect, the invention provides a method of detecting one or more mutations in a receptor tyrosine kinase (RTK), the method comprising the steps of:
(i) providing a test sample containing cells expressing the RTK;
(ii) imaging RTK molecules at the cell surface;
(iii) determining the nanometre (nm) spatial separation between RTK molecules assembled in any RTK oligomer(s) located at the cell surface;
(iv) comparing the nanometre (nm) spatial separation determined in (iii) with the nanometre (nm) spatial separation determined for equivalent RTK molecules assembled in any RTK oligomer(s) located at the cell surface in a control sample,
wherein the comparison between control and test sample is used to determine the presence of one or more mutations in the RTK in the test sample.

Since aberrant RTK activation and the presence of mutations in RTKs has been linked with the development of a number of diseases, notably cancer, methods based on imaging of RTK molecules at the cell surface are described herein for use in methods directed to various aspects of disease prognosis, diagnosis and treatment.

In one aspect, the invention provides a method of determining prognosis for a subject having a disease characterised by aberrant RTK activation, the method comprising the steps of:
(i) isolating a sample containing cells from said subject;
(ii) imaging RTK molecules at the cell surface;
(iii) determining the presence of one or more RTK oligomers wherein the RTK oligomers comprise more than two RTK monomers,
and wherein the one or more RTK oligomers is/are indicative of prognosis in said subject.

In a further aspect, the invention provides a method of determining prognosis for a subject having a disease characterised by aberrant RTK activation, the method comprising the steps of:
(i) isolating a test sample containing cells from said subject;
(ii) imaging RTK molecules at the cell surface;
(iii) determining the nanometre (nm) spatial separation between RTK molecules assembled in any RTK oligomer(s) located at the cell surface;
(iv) comparing the nanometre (nm) spatial separation determined in (iii) with the nanometre (nm) spatial separation determined for equivalent RTK molecules assembled in any RTK oligomer(s) located at the cell surface in a control sample, wherein the control sample contains cells expressing RTK molecules that are not aberrantly activated,
and wherein a difference in the nanometre spatial separation between RTK molecules assembled in any RTK oligomer(s) in the test sample as compared with the control sample is indicative of prognosis in said subject.

In a further aspect, the present invention provides a method of selecting a subject for treatment with a RTK inhibitor, the method comprising the steps of:
(i) isolating a sample containing cells from a subject;
(ii) imaging RTK molecules at the cell surface;
(iii) determining the presence of one or more RTK oligomers wherein the RTK oligomers comprise more than two RTK monomers,
and the RTK molecules that are imaged are the target of the RTK inhibitor.

In all aspects of the invention, in certain embodiments, the RTK molecules are imaged using a high-resolution imaging method, preferably a high-resolution imaging method capable of determining intermolecular distances in the range from about 5 nm to about 80 nm, preferably wherein the high-resolution imaging method is Fluorophore Localisation Imaging with Photobleaching (FLImP).

In all aspects of the invention, in certain embodiments, the RTK oligomers are selected from tetramers, hexamers, or higher-order oligomers consisting of at least 8, at least 10, at least 12, at least 14, at least 16, at least 18, at least 20 RTK monomers, preferably wherein the RTK oligomers are tetramers.

In all aspects of the invention, in certain embodiments, the RTK is selected from: EGFR, ErbB2, ErbB3 and ErbB4, preferably EGFR.

DETAILED DESCRIPTION

A. Definitions

Figure 1:
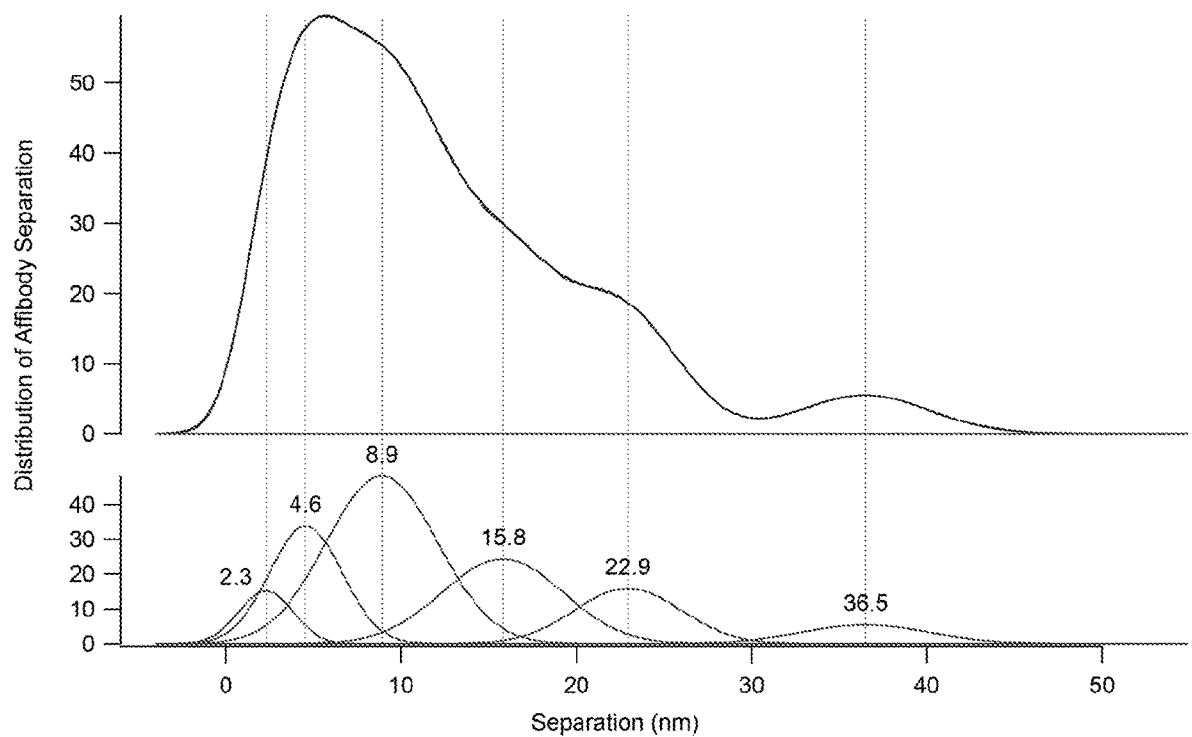
FIG. 1 Results of imaging carried out to detect the spatial separation of EGFR molecules on CHO cells. EGFR molecules were labelled with 9G8 affibody conjugated with the fluorescent dye CF640R. The affibody binds to EGFR but does not activate it, allowing measurement of the basal state. Cells were labelled with the affibody-dye conjugate, fixed with paraformaldehyde/glutaraldehyde, and intermolecular separations measured using Flurophore Localisation Imaging with Photobleaching (FLImP). The upper plot shows the histogram of separations, while the lower plot shows gaussian peaks fitted to the histogram, indicating the separations measured. Analysis shows multiple separations, corresponding to inactive complexes (2.3, 4.6, and 8.9 nm) and higher order oligomers.
Figure 2:
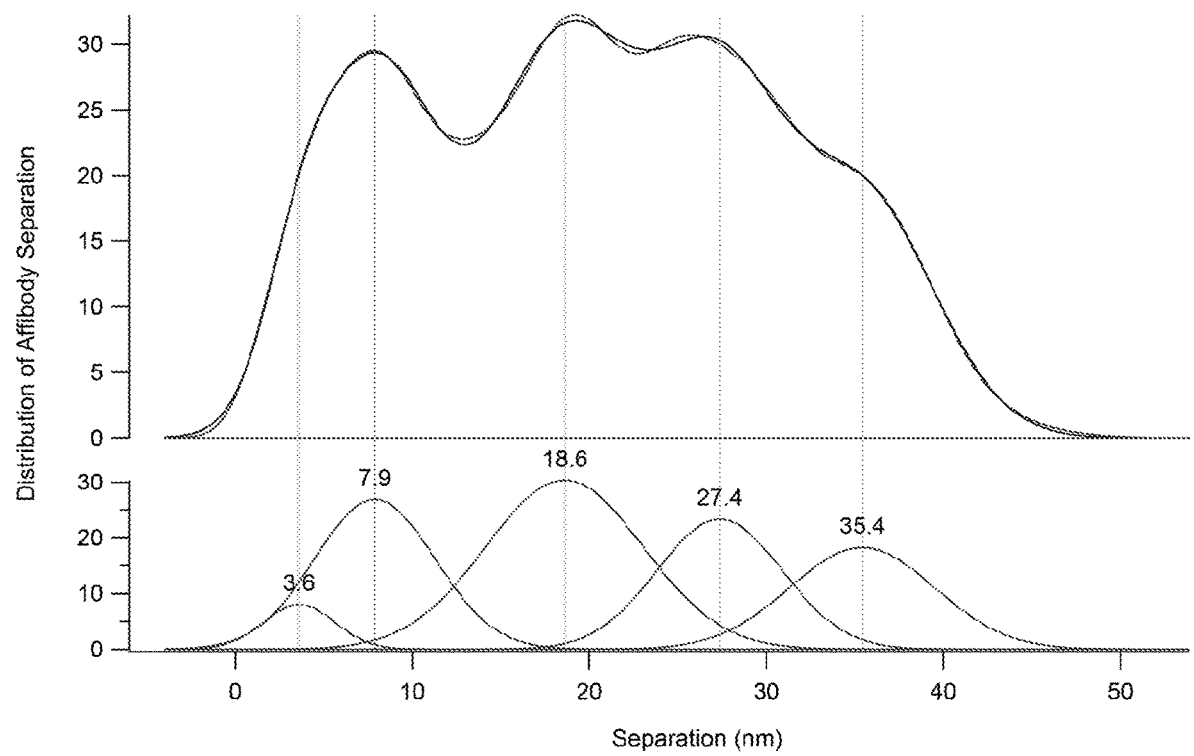
FIG. 2 Results of a FLImP measurement on EGFR in cells, activated by EGF at physiological concentration. EGF was conjugated with the fluorescent dye CF640R, and the EGF-dye conjugate was added to CHO cells at a concentration of 4 nM. Cells were fixed with paraformaldehyde/glutaraldehyde and spacings between EGFR measured using FLImP. Analysis shows short spacings corresponding to inactive complexes (3.6 and 7.9 nm), active dimers (18.6 nm), hexamers (27.4 nm) and higher order oligomers.

Unless defined otherwise, all technical and scientific terms used herein have the same meaning as commonly understood by the ordinary person skilled in the art to which the invention pertains. Without limiting any term, further clarifications of some of the terms used herein are provided below.

"Receptor tyrosine kinase" or "RTK"—as used herein, the term "receptor tyrosine kinase" or the abbreviation "RTK" is intended to mean any integral cell membrane-spanning protein capable of binding ligand in the wild-type form and possessing intrinsic tyrosine kinase activity. RTKs have a characteristic molecular architecture consisting of an extracellular region, a transmembrane domain which is typically a single transmembrane helix, and a cytoplasmic or intracellular region. The extracellular region may be composed of one or more domains that accommodate ligand binding. Such domains include but are not limited to: immunoglobulin domains, cysteine-rich domains, leucine-rich domains, fibronectin type III domains, kringle domains, ephrin binding domains, WIF domains, Sema domains, L domains. The cytoplasmic or intracellular (used herein interchangeably) region typically includes the tyrosine kinase domain (abbreviated to "TKD") and may additionally include a juxtamembrane regulatory region and/or a C-terminal region.

Twenty subfamilies of RTK have been described in humans as shown in Table 1 below. Each of the RTK subfamilies described in the literature includes one or more receptors having specificity for a particular ligand or a particular subset of activating ligands. The term "RTK" as used herein is intended to encompass all of the human RTKs identified in Table 1.

TABLE 1

Human Receptor Tyrosine Kinase subfamilies

| Subfamily | Receptors |
| --- | --- |
| ErbB/EGFR | EGFR, ErbB2, ErbB3, ErbB4 |
| Ins | InsR, IGF1R, InsRR |
| PDGF | PDGFRα, PDGFRβ, CSF1R/Fms, Kit/SCFR, Flt3/Flk2 |
| VEGF | VEGFR1/Flt1, VEGFR2/KDR, VEGFR3/Flt4 |
| FGF | FGFR1, FGFR2, FGFR3, FGFR4 |
| PTK7 | PTK7/CCK4 |
| Trk | TrkA, TrkB, TrkC |
| Ror | Ror1, Ror2 |
| MuSK | MuSK |
| Met | Met, Ron |
| Axl | Axl, Mer, Tyro3 |
| Tie | Tie1, Tie2 |
| Eph | EphA1-8, EphA10, EphB1-4, EphB6 |
| Ret | Ret |
| Ryk | Ryk |
| DDR | DDR1, DDR2 |
| Ros | Ros |
| LMR | LMR1, LMR2, LMR3 |
| ALK | ALK, LTK |
| STYK1 | SuRTK106/STYK1 |

Various mutations have been identified in the genes encoding wild-type RTKs, particularly in cancer cells. Such mutations can lead to RTK overexpression and in some cases lead to changes in the amino acid sequence of the native RTK. Mutant RTKs have been described having amino acid substitutions, insertions, deletions and/or truncations of portions of the extracellular or intracellular regions. The term "mutation" as used herein in connection with the RTK protein should be taken to mean any of the structural modifications described above for mutant RTKs. Mutant or "non-native" RTKs i.e. variants of the wild-type RTKs, particularly those associated with cancer, are within the scope of the term "RTK" as used herein.

"Monomer"—as used herein, the term "monomer" means a single RTK protein having the core elements of: (i) an extracellular region; (ii) a transmembrane segment; and (iii) an intracellular region. The protein may be truncated or otherwise modified as compared with the corresponding wild-type form of the protein as described above. In the context of the present invention, the term "monomer" or "receptor monomer" is used interchangeably with receptor "molecule" or receptor "subunit". In the absence of activating ligand, many RTKs exist as inactive monomers in the cell membrane, for example the EGFR typically exists as monomers in the cell membrane of unstimulated cells. As explained below, these monomers can associate into higher-order receptor complexes, consisting of two or more receptor subunits, particularly in response to ligand binding.

"Dimer"—as used herein, the term "dimer" means a complex consisting of two receptor monomers or subunits. A dimer may form through the covalent binding of two receptor monomers as in the case of the insulin receptor and IGF1 receptor, which form disulphide-linked dimers. Alternatively, dimers can form through the non-covalent association of one or more complementary binding interfaces on each receptor monomer. RTK dimers may be "homodimers" wherein the two monomers forming the dimer are identical or may be "heterodimers" wherein the two monomers forming the dimer are different. The EGFR family of receptors is an example of a family wherein homodimers and heterodimers can form. RTK dimers may be described as "inactive" or may be "active" wherein activation typically occurs upon ligand binding. As noted above, the insulin receptor and IGF1 receptor exist as disulphide-linked dimers on the cell surface in the absence of ligand, but are present in an inactive state or conformation such that there is no signalling downstream of the receptor. An "active dimer" refers to a dimer having a distinct conformation that permits activation of the tyrosine kinase domain in the intracellular region of at least one of the receptor monomers. As explained below, activation typically occurs upon ligand binding to the extracellular region of at least one of the receptor monomer subunits of the dimer. Activation can also occur in the absence of ligand in the case of some mutant RTKs.

"Oligomer"—as used herein, the term "oligomer" means a complex or assembly of more than two receptor monomers or subunits. The receptor monomers in the oligomer may be held together by covalent bonds, for example disulphide bridges. Alternatively, the receptor monomers in the oligomer may be associated via one or more complementary binding interfaces on each receptor monomer. An oligomer in accordance with the present invention may have at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 monomer subunits. RTK oligomers may include complexes or assemblies formed of multiple RTK dimers and thus may be selected from tetramers, hexamers, octamers or higher-order oligomers consisting of 10, 12, 14, 16, 18, 20, 22, 24, 26, 28, 30 monomers.

"RTK Activation"—as used herein, the term "RTK activation" is intended to mean the structural or conformational changes that occur upon ligand binding to RTKs and in particular, the conformational changes that result in activation of the tyrosine kinase domain in the intracellular region(s) of the receptor and the autophosphorylation of receptor tyrosine residues. In the "active" state, the tyrosine kinase domain of an RTK is activated.

RTKs are activated by ligand binding to the extracellular region of the molecule and for RTKs that exist as monomers in the inactive state, ligand binding typically induces dimerisation. The means by which the binding of ligand induces receptor dimerisation differs between different members of the RTK family. In some cases, dimerisation is mediated via a bivalent ligand that binds simultaneously to the two receptor monomers thereby bringing them into close proximity. In other situations, ligand binding to a receptor monomer brings about a conformational change in the extracellular region of the receptor thereby facilitating dimer formation, for example by the exposure of an interface allowing for receptor association. The EGFR forms a so-called "back-to-back dimer" wherein the two EGF ligands bind to the extracellular region of each monomer at sites distal from the dimer interface.

Irrespective of the means by which ligand binding induces dimerisation, activation requires propagation of a conformational change through the molecule such that the tyrosine kinase domain in the intracellular region is activated. In the inactive conformation, the tyrosine kinase domain of each RTK is cis-autoinhibited by a portion of the intracellular region and activation requires release of this cis-autoinhibition. The mechanism by which autoinhibition is released following receptor activation can vary between members of the RTK family. In many cases, activation of the tyrosine kinase domain is achieved or stabilised by trans-phosphorylation of one or more critical tyrosine residues in the activation loop of the TKD itself. Trans-phosphorylation means phosphorylation of one or more tyrosine residue(s) on one receptor monomer unit by the TKD of another receptor monomer. Phosphorylation of tyrosine residues in the juxtamembrane region and/or the C-terminal region of the intracellular region can also aid in stabilising the active conformation of the receptor. The activated form of the receptor can also be maintained as a result of allosteric effects at the level of the intracellular domain mediated by ligand binding to the extracellular region. Once an RTK is activated, one or more (additional) tyrosine (Tyr) residues within the intracellular region are typically autophosphorylated thereby triggering a chain of downstream signalling events, as described below.

"Aberrant RTK Activation"—as used herein, the term "aberrant RTK activation" or "dysregulated RTK activation" means an RTK activation status that differs from normal or that differs from the degree of RTK activation expected under normal physiological conditions. Aberrant RTK activation typically occurs as a result of a defect in the normal processes regulating RTK activation in response to ligand binding. Such a defect may arise as result of a defect in RTK expression such that the expression of RTK protein is increased or decreased relative to normal. Such a defect may also arise as a result of a mutation in an RTK that alters the way in which the RTK is activated by ligand. For example, mutations have been observed in RTKs in cancer cells that lead to constitutive activation of the RTK in the absence of ligand binding. Aberrant RTK activation thus encompasses constitutive RTK activation.

"RTK Signalling"—as used herein, the term "RTK signalling" is intended to mean the chain of signalling events that occur once an RTK has been activated by ligand binding. As described above, one of the first events to happen following RTK activation is the autophosphorylation of one of more tyrosine residues within the intracellular region of the receptor itself. These phospho-tyrosine (pTyr) residues can serve as docking sites for proteins containing "SH2" or "PTB" domains, on the basis that these domains specifically recognise and bind pTyr residues. It follows that activated RTKs can serve as platforms for the binding of a variety of cell signalling proteins. The recruitment of proteins to the cell membrane via interactions mediated by receptor pTyr residues typically triggers a cascade of downstream signalling pathways, many of which are well characterised in the literature. Signalling pathways that are activated downstream of activated RTKs include, but are not limited to, the phosphatidylinositol-3-kinase (PI3K)—Akt pathway, the Ras-MAPK pathway, the phospholipase Cγ-protein kinase C pathway and the Jak/STAT pathway.

"EGFR" and "EGFR family"—as used herein, "EGFR" means the Epidermal growth factor receptor. This receptor was one of the first RTKs to be identified and may also be referred to as the ErbB or ErbB1 receptor. EGFR is closely related to three other RTKs found in humans, ErbB2/HER2, ErbB3/HER3 and ErbB4/HER4, and together, these four RTKs form the EGFR family. The EGFR family receptors share a common structure consisting of an extracellular region of approximately 620 amino acids having four separate domains, a transmembrane domain of approximately 23 amino acids and a large intracellular region of approximately 540 amino acids. The intracellular region is characterised by a short juxtamembrane region, a TKD and a largely unstructured C-terminal tail consisting of approximately 230 amino acids. Following activation of the EGFR family receptors, a series of tyrosine residues in the C-terminal tail become autophosphorylated in trans and serve as docking sites for the downstream signalling proteins described above.

"RTK Inhibitor"—as used herein, the term "RTK inhibitor" means any agent capable of inhibiting the intrinsic tyrosine kinase activity of RTKs. The term "inhibitor" is intended to be broad enough to encompass any form of inhibitory molecule including, but not limited to, inhibitory nucleic acid species (for example siRNA molecules), antibodies and small-molecules. Several RTK inhibitors have already been developed and approved for use in cancer treatment and there are many more in various stages of clinical development. Table 2 below lists a number of the known RTK inhibitors.

TABLE 2

RTK inhibitors approved or in development for treating cancer

| Inhibitor | RTK Target | Type of drug |
|---|---|---|
| Imatinib (Gleevec) | c-KIT, PDGFR | Small molecule |
| Gefitinib (Iressa) | EGFR | Small molecule |
| Erlotinib (Tarceva) | EGFR | Small molecule |
| Lapatinib | EGFR, ErbB2 | Small molecule |
| Canertinib | EGFR | Small molecule |
| Semaxinib | VEGFR-2, c-KIT, FLT-3 | Small molecule |
| Vatalanib | VEGFR-1 | Small molecule |
| Sunitinib (Sutent) | VEGFR, PDGFR, c-KIT, FLT-3 | Small molecule |
| Sorafenib | VEGFR-2, PDGFR | Small molecule |
| Leflunomide | PDGFR | Small molecule |
| Busotinib (Bosulif) | HER3 | Small molecule |
| Trastuzumab (Herceptin) | HER2 | Antibody |
| Bevacizumab (Avastin) | VEGFR | Antibody |
| Cetuximab (Erbitux) | EGFR | Antibody |
| Panitumumab (Vectibix) | EGFR | Antibody |
| Nanobodies | Various | Antibody |
| Bispecific antibodies (e.g. Catumaxomab) | Various | Antibody |

"Imaging"—as used herein, the term "imaging RTK molecules" means the direct or indirect visualisation of RTK molecules at the cell surface. Many different microscopy techniques are available for imaging cells and in particular molecules located in or on cells including but not limited to immune-electron microscopy, fluorescence microscopy, atomic force microscopy, photoactivated localisation microscopy, stochastic optical reconstruction microscopy, stimulated emission depletion and near-field scanning optical microscopy.

"Fluorophore Localisation Imaging with Photobleaching (FLImP)"—as used herein, the term "Fluorophore Localisation Imaging with Photobleaching", abbreviated to "FLImP", refers to a specific high-resolution imaging technology, which can be used to study the spatial separation between individual proteins, for example the separation between RTKs, located within the cell membrane. This separation between RTK molecules may also be described as the "intermolecular distance" between RTK molecules. The FLImP technique as referred to herein is described for example in the following publication: Needham et al. Measuring EGFR separations on cells with ~10 nm resolution via fluorophore localization imaging with photobleaching. PLoS One. 2013 May 1; 8(5): e62331 (the contents of which are incorporated herein in their entirety).

FLImP is an imaging technique that can be used to image at high-resolution, typically at a resolution of 7 nm or better. This imaging technique can be used to measure intermolecular distances in the 5-80 nm range. This range is particularly important for the study of RTK oligomer formation because the spatial separation between individual receptor monomers in an oligomer typically falls within this range.

B Receptor Tyrosine Kinase (RTK) Oligomers as Biomarkers

The present invention is based on the surprising observation that RTK oligomers are required for optimal receptor autophosphorylation in the presence of physiological ligand concentrations. This indicates that such RTK oligomer complexes operate as functional signalling complexes at the cell surface. Although it has been known for many years that ligand-induced dimerisation is required for RTK activation and signalling, the structure and role of RTK oligomers at the cell surface has remained unclear. The discovery reported herein that RTK oligomers promote receptor autophosphorylation and thereby play a key role in RTK activation identifies such RTK oligomers as structural markers or "biomarkers" for use in the different aspects of the invention described herein.

In particular, the present invention provides in different aspects, a variety of methods that are directed to: (i) monitoring RTK activation; (ii) detecting one or more mutations in a RTK; (iii) determining patient prognosis for subjects having diseases characterised by aberrant RTK activation; and (iv) selecting subjects for treatment with RTK inhibitors.

In all aspects of the invention described herein, the basic methodology is the same and involves imaging RTK molecules at the cell surface. RTK molecules are imaged, preferably using high-resolution technology, so as to determine the nanometre (nm) spatial separation between RTK molecules and/or to determine the presence of RTK oligomers at the cell surface. Information relating to the spatial separation of RTK molecules and/or the presence of one or more RTK oligomers can be interpreted for use in the applications described below.

C Imaging RTK Molecules

The methods of the present invention involve the imaging of RTK molecules located at the surface of cells. As described above, RTKs are integral membrane proteins having extracellular and intracellular regions. The imaging of RTK molecules at the cell surface means the detection of RTK molecules located within the cell membrane at the cell periphery.

RTK molecules are imaged according to the present invention so as to determine the presence of one or more RTK oligomers at the cell surface. Preferably, the one or more RTK oligomers are identified and/or characterised by determining the nanometre (nm) spatial separation between RTK molecules at the cell surface. The presence of RTK oligomers and their distinct structure i.e. the precise spatial separation between RTK molecules, are markers linked to RTK mutations, activation and signalling in cells, and can thus be informative in the multiple aspects of the invention described herein.

The methods as described herein are based on the imaging of one or more cells, typically wherein the imaging is carried out in vitro on a cell culture. The cells to be imaged may be taken from a sample of cells isolated from a subject and may derive from any suitable tissue or organ depending on the nature of the analysis. In certain embodiments, imaging may be carried out on a cell population or cell sample known to express the RTK of interest or suspected of expressing the RTK of interest.

In the methods described herein, imaging may be carried out on cells derived from a sample taken from a subject diagnosed with a particular disease or disorder associated with aberrant RTK activation, or a subject suspected of having such a disease or disorder. In such embodiments, the sample containing cells for analysis may be isolated from a diseased tissue or site in the body. For example, if the sample is being taken from a subject suspected of having cancer or diagnosed with cancer, the sample containing cells may be taken from the affected site in the body. In certain embodiments, the sample containing cells for analysis is a tumour biopsy taken from an affected site in the body.

The sample containing cells for analysis may be processed using any technique compatible with the imaging technology to be used. For example, the sample or cells derived from the sample may be cryopreserved or fixed using any suitable technique known to those skilled in the art. Alternatively or in addition, the sample may be labelled or stained using reagents required for imaging. As described herein below, preferred imaging techniques for use in the methods described herein are based on fluorescence imaging and in particular, detecting the photobleaching of fluorophores associated with RTKs in the cell membrane. Therefore, prior to imaging, the sample or cells therein may be treated with one or more fluorescent reagents required for imaging. Any suitable fluorescent reagent or fluorophore known to those skilled in the art may be used in conjunction with the imaging techniques described herein.

If the sample containing cells is processed prior to imaging, any techniques used should aim to preserve the structure of any oligomeric receptor complexes formed at the cell surface. This should allow for more accurate study of any RTK oligomers present at the cell surface.

The imaging of cells as required by the present methods can be carried out using any suitable imaging technique. The imaging method is required to be "high-resolution" wherein high-resolution means a method capable of achieving a level of resolution allowing for the determination of RTK molecule separation on the surface of cells at the nanometre level. In certain embodiments, the imaging method or high-resolution imaging method used is capable of determining intermolecular distances in the range from about 5 nm to about 80 nm.

A particularly suitable technique for use in conjunction with the methods described herein is Fluorophore Localisation Imaging with Photobleaching or "FLImP", which has been previously described, for example in Needham et al. Measuring EGFR separations on cells with ~10 nm resolution via fluorophore localization imaging with photobleaching. PLoS One. 2013 May 1; 8(5): e62331 (the contents of which are incorporated herein in their entirety).

The FLImP technique allows the spatial separation between RTK molecules to be determined with a resolution of 7 nm or better based on the single-step photobleaching of fluorophores associated with the individual RTK molecules located in the cell membrane. The flurophores may be associated directly or indirectly with membrane-localised RTK molecules. For embodiments wherein the fluorophore is associated indirectly, the fluorophore may be conjugated to a ligand that is capable of binding to the RTK of interest. Any suitable RTK ligand conjugated to a fluorophore may be used for imaging purposes. In preferred embodiments, RTK molecules are imaged at the cell surface using Fluorophore Localisation Imaging with Photobleaching wherein the imaging is carried out using RTK ligands labelled with one or more fluorophores. Any suitable fluorophores known to the person skilled in the art may be used in conjunction with the FLImP technique.

RTK molecules may be imaged according to the present methods so as to determine the nanometre (nm) spatial separation between RTK molecules. As described in the Examples section below, determination of the nanometre spatial separation between RTK molecules can permit the identification and characterisation of RTKs organised as oligomers in the cell membrane. One means for translating this spatial separation information into a read-out of RTK oligomer status is to (i) determine the spatial separation between RTK molecules configured as a dimer; and (ii) determine if one or more additional RTK molecules are detectable at a distance that would be incompatible if the additional one or more RTK molecules were not associated with the RTK molecules of the dimer in a higher-order oligomer complex.

The precise spacing or intermolecular distances between RTK molecules in any given RTK oligomer complex may vary slightly depending on the packing and/or arrangement of the monomer and/or dimer units within the higher-order oligomer complex. It follows that the nanometre spatial separation between RTK molecules assembled as oligomers may, in and of itself, be indicative of RTK activation in a sample.

The precise spacing or intermolecular distances between RTK molecules can be affected by the presence of one or more mutation(s) in the RTK molecules packed and/or arranged within any given oligomer complex. As explained in more detail below, information about the nanometre spatial separation of RTK molecules in an oligomer can thus be used to detect the presence of one or more mutations in a given RTK in a particular sample.

Imaging of RTK molecules is carried out to determine the presence of one or more RTK oligomers at the cell surface. As explained above, the term "RTK oligomers" is used herein to mean RTK complexes or assemblies comprising or consisting of more than two RTK monomer subunits. The methods of the present invention may be carried out to determine the presence of one or more RTK oligomers in order to provide information about the status of RTK activation and signalling in cells. The precise quantity and distribution of RTK oligomers assessed may depend on the purpose of the analysis as explained below.

For the purposes of determining whether a particular RTK is activated in a particular cell type, it may be adequate to observe the presence of one or more RTK oligomers in a cell sample. In certain embodiments, the methods may involve detecting the presence of one or more RTK oligomers in a given number of cells in the sample, for example one or more RTK oligomers per cell, per two cells, per five cells, per 10 cells, per 20 cells, per 30 cells. For the analysis of patient samples, it may be necessary to detect the presence of multiple RTK oligomers wherein multiple is used herein to mean two or more, three or more, four or more, five or more, six or more, seven or more, eight or more, nine or more, ten or more etc. Quantitation of RTK oligomers may be based on a calculation per cell or for a given number of cells in a sample.

The methods of the present invention may be carried out to detect the presence of one or more RTK oligomers wherein an "oligomer" takes any of the forms described above. For example, the methods may involve detection of complexes consisting of at least 3, at least 4, at least 5 up to at least 20 monomer units. In preferred embodiments, the RTK oligomers are higher-order assemblies of receptor dimers and are therefore selected from tetramers, hexamers and/or octamers, most preferably tetramers.

In addition to determining the presence of one or more RTK oligomers, the methods described herein may comprise a step of determining or characterising the nanometre spatial separation between RTK molecules assembled within any RTK oligomer complexes located at the cell surface. This information relating to the spatial separation of RTK molecules may be used to monitor RTK activation. For example, the spatial separation of RTK molecules assembled as one or more RTK oligomers measured for one cell sample may be compared with information obtained from the imaging of equivalent RTKs at the cell surface using one or more control or reference sample(s). This comparison may allow differences in RTK activation to be detected between, for example, a control and test sample.

As used herein in the context of comparative methods, the term "equivalent RTK" means the same type of RTK as the RTK under test. For example, if the RTK analysed in the test sample is EGFR, the "equivalent RTK" in the control or reference sample is also EGFR. The EGFR molecules in the control/reference sample and test sample may not be identical in sequence because the purpose of the comparison is typically to identify any differences between the two. However, "equivalent RTK" means the same RTK protein or the RTK protein encoded by the equivalent gene in the cells of the control sample.

The methods of the present invention may be carried out to detect oligomers formed from any RTKs, particularly any of the RTKs belonging to the 20 subfamilies identified in Table 1. The RTKs may be native or wild-type forms of the RTK or may be mutated, for example RTKs found in cancer cells. In preferred embodiments of the invention, the methods are carried out to image and/or detect oligomers formed from RTKs of the EGFR family wherein the EGFR family includes EGFR (or ErbB1), ErbB2, ErbB3 and ErbB4. In such embodiments, the RTK oligomers may be homo-oligomers i.e. oligomers including only one type of EGFR family monomer, or may be hetero-oligomers including at least two different types of EGFR family monomer. In particularly preferred embodiments, the methods involve imaging EGFR molecules (or ErbB1 molecules) for the purposes of detecting the presence of one or more EGFR oligomers (or ErbB1 oligomers).

As described in the Examples section below, the present inventors have used FLImP imaging technology to characterise the spatial separation between EGFR molecules organised in the cell membrane as EGFR dimers and oligomers. A spatial separation of approximately 11-13 nm has been found to be characteristic of the formation of an active wild-type EGFR dimer. Spatial separations measured at approximately 18-20 nm, particularly at approximately 18 nm, have been identified as indicative of the presence of EGFR tetramers. Thus, in certain embodiments, the methods as described herein involve the imaging of EGFR molecules at the cell surface, particularly using FLImP, and detection of one or more EGFR tetramers on the basis of a spatial separation of EGFR molecules measured at approximately 18-20 nm, particularly at approximately 18 nm. In certain embodiments, EGFR oligomers are detected by measuring the spatial separation of EGFR molecules, wherein a spatial separation of approximately 11-13 nm indicates the presence of an active dimer and additional spatial separations measured at 6-9 nm intervals indicate the presence of one or more dimer units in a high-order oligomer structure.

The spatial separation between RTK molecules can be measured directly or indirectly. For embodiments wherein FLImP is used as the imaging technique, the spatial separation between RTK molecules is calculated using fluorescence photobleaching. In certain embodiments, the fluorophores used for imaging are conjugated to one or more ligands that bind to the extracellular region(s) of the RTK molecules of interest. For embodiments wherein EGFR or EGFR family RTKs are imaged, the fluorophore(s) may be conjugated to any suitable EGF family ligands including, but not limited to, EGF, TGFα, ARG, EGN, HB-EGF, EPR, BTC, NRG1, NRG2, NRG3 and/or NRG4.

The techniques described above for imaging RTK molecules and oligomers located at the surface of cells can be applied in a variety of different settings according to the methods described herein below. All embodiments described above in relation to the detection of RTK molecules and oligomers at the cell surface are applicable to the various aspects of the invention described in sections D, E and F.

D Monitoring Receptor Tyrosine Kinase (RTK) Activation

At a fundamental level, the imaging of RTK oligomers can be used to monitor RTK activation in cells. As used herein, the term "monitor" means studying RTK activation in cells, in particular to determine whether the RTK is inactive, active, or to determine whether activation is altered as compared with an RTK having a known activation state. The present inventors have shown for the first time that ligand-induced RTK oligomers formed at the cell surface are required for optimal receptor autophosphorylation and therefore play an essential role in optimal RTK activation and signalling. The inventors have further shown that the nanometre spatial separation between RTK molecules organised as RTK oligomers is indicative of RTK activation.

Therefore, in a first aspect of the present invention, RTK oligomers formed at the cell surface are used as markers by which to monitor RTK activation in a cell.

As explained above, RTK activation typically occurs upon ligand binding to the extracellular region of a RTK. Ligand binding is accompanied by conformational changes in the receptor that lead to activation of the tyrosine kinase domain in the intracellular region. Activation of all RTKs is accompanied by autophosphorylation of one or more tyrosine residues located within the intracellular region of the receptor. Autophosphorylation typically occurs "in trans" wherein the TKD of one subunit acts to phosphorylate one or more tyrosine residues in the intracellular region of a different or adjacent RTK subunit within a dimeric or oligomeric complex.

In the methods of the present invention, RTK activation may be characterised by the phosphorylation of one or more, two or more, three or more, four or more, five or more, six or more tyrosine or threonine residues in the intracellular region. The phosphorylated residues may be located in any part of the intracellular region including the juxtamembrane region, the TKD and/or the C-terminal region or tail. In certain embodiments (e.g. EGFR), the phosphorylated residues may be selected from: Tyr 845, Tyr 992, Tyr1045, Tyr 1068, Tyr1148 and Tyr 1173.

RTK activation may also be characterised by an increase in activity of the tyrosine kinase domain, such that downstream effector proteins are phosphorylated. Activation of the TKD can be measured directly or indirectly using standard assays known to those skilled in the art, for example assays designed to measure kinase activity by detecting phosphorylation of substrate proteins.

The methods of the present invention are preferably carried out to monitor activation of members of the EGFR family, particularly the EGFR itself. The EGFR family RTKs undergo a distinct conformational change upon ligand binding and dimerisation such that the intracellular regions of opposed EGFR monomers adopt an "assymetric dimer" leading to tyrosine kinase activation. In this asymmetric dimer, the carboxy region of one TKD—the "activator kinase"—abuts the amino region of the other TKD—the "receiver kinase"—such that the receiver is allosterically activated. The receiver kinase then autophosphorylates the activator kinase, particularly at tyrosine residues within the C-terminal tail. The present inventors have now shown that EGFR oligomerisation is essential for optimal autophosphorylation of EGFR following activation. The methods as described herein are thus particularly suitable for monitoring activation of members of the EGFR family.

Information about RTK activation may be determined from the presence of one or more RTK oligomers and/or the nanometre (nm) spatial separation between RTK molecules assembled as RTK oligomers, for any given cell sample. Ligand-induced RTK oligomer formation is required for optimal RTK autophosphorylation at physiological ligand concentration. Thus in certain embodiments, the presence of one or more RTK oligomers is/are indicative of RTK activation. In certain embodiments, RTK activation may be assessed by comparing the nanometre spatial separation of RTK molecules assembled as RTK oligomers in a test sample with the spatial separation of equivalent RTK molecules assembled as RTK oligomers in a control or reference sample, wherein a difference between the two samples is indicative of differential RTK activation in the test sample. In such embodiments, the control sample may contain cells having an RTK with a known activation status or signalling capacity thereby allowing the RTK activation status of the test sample to be determined relative to control.

E Detecting Receptor Tyrosine Kinase (RTK) Mutations

Imaging of RTK molecules can also be used to detect one or more mutations in an RTK, in particular by comparing the results obtained from two or more different cell-containing samples. As noted above, the precise spatial separation between RTK molecules within an oligomer complex may be affected by mutations in the RTK molecules, or more specifically mutations in the encoding nucleic acid sequence that affect the resultant amino acid sequence of the protein. An RTK mutation may be a change in amino acid sequence selected from any of the following: insertion(s) of one or more amino acids, deletion(s) of one or more amino acids and/or substitution(s) of one or more amino acids. Such changes may occur anywhere along the length of the RTK protein, preferably in the intracellular domain.

One aspect of the present invention provides methods for detecting one or more mutations in a RTK in a test sample containing cells expressing the RTK. In certain embodiments, the methods involve detection of two or more, three or more, four or more, five or more, six or more, seven or more, eight or more, nine or more, ten or more mutations in a RTK in a test sample.

Methods carried out so as to determine the presence of one or more RTK mutations involve a comparison of the imaging results obtained using at least one test sample and at least one control sample. The control sample is a sample containing cells having the wild-type form of the equivalent RTK expressed by the test sample or another reference form of the RTK.

In a first stage of the method, the RTK molecules at the cell surface are imaged and the nanometre spatial separation between RTK molecules assembled as an oligomer is determined. In a second stage of the method, the result obtained in the first stage is compared with the results obtained by imaging cells in a control sample. In certain embodiments, the control sample contains cells expressing the wild-type form of the RTK. In such embodiments, if the spatial separation observed between RTK molecules assembled as a oligomer is different between the test and control samples, this may be indicative of one or more mutations in the RTK in the test sample. In certain embodiments, the control sample contains cells expressing a reference RTK wherein a reference RTK is a known mutant form of the RTK. In such embodiments, if the spatial separation observed between RTK molecules assembled as a oligomer is the same between test and control samples, this may be indicative of the same RTK mutant in the test sample as found in the control sample. Alternatively, if the spatial separation observed between RTK molecules assembled as a oligomer is different between test and control samples, this may be indicative of the absence of the mutant RTK in the test sample.

The mutations detected according to the methods described herein may affect activation of the RTK. For example, the mutations may increase or decrease activation of the RTK. The methods described herein based on the detection of one or more mutations in a RTK may thus be used to indirectly monitor RTK activation in cells.

F. Receptor Tyrosine Kinase (RTK) Oligomers as Biomarkers in Disease

As explained above, dysregulated RTK activation and signalling, particularly increased RTK activation and signalling, has been associated with a number of diseases including but not limited to cancer, diabetes, cardiovascular disease including atherosclerosis, inflammatory disorders, bone disorders, neurodegenerative diseases including Alzheimer's disease and motor neurone disease, and arthritis. The observation reported herein linking RTK oligomers to RTK activation opens up the possibility of using RTK oligomers as biomarkers for monitoring multiple aspects of disease prognosis and treatment.

The term "biomarker" or "biological marker" typically refers to a measurable indicator that correlates with a particular biological state. In the context of disease, a biomarker is typically a characteristic that can be objectively measured and may be correlated with or indicative of any aspect of disease onset, development or treatment including, but not limited to, the following: (i) a patient's risk of developing disease (a risk biomarker); (ii) the presence of disease in an individual (a diagnostic biomarker); (iii) disease progression or severity in an individual (a prognostic biomarker); (iv) the pharmacological response to a therapeutic agent.

Many different forms of biomarker have been described in the literature, for example genetic biomarkers, protein biomarkers, metabolic biomarkers. Protein markers are often detected or measured at the protein expression level, for example circulating levels of a particular protein in the blood of a patient. The RTK oligomers for detection according to the methods of the present invention may be considered "structural biomarkers" on the basis that it is the organisation or conformation of these receptor complexes that provide a read-out correlating with RTK activation at the surface of cells. These structural biomarkers can be detected using the imaging techniques described elsewhere herein, and are beneficial in the multiple settings described below.

Disease Prognosis

In particular aspects, the present invention provides methods of determining prognosis for a subject having a disease characterised by aberrant RTK activation. Such methods may involve imaging RTK molecules at the surface of cells in a sample isolated from said subject and determining the presence of one or more RTK oligomers, wherein the presence of one or more RTK oligomers is indicative of prognosis.

Alternatively, or in addition, such methods may involve imaging RTK molecules at the surface of cells in a sample isolated from a subject, determining the nanometre spatial separation of RTK molecules assembled as an oligomer and comparing the spatial separation or intermolecular distances measured with the distances measured using a control sample. The control sample will typically contain cells expressing RTK wherein the RTK molecules are not aberrantly activated. Any differences observed between the nanometre spatial separation of RTK molecules assembled as an oligomer in the test sample as compared with the control sample may be indicative of prognosis in said subject.

Prognostic methods as described herein may also be carried out on two or more test samples isolated from a subject over a defined period of time or at defined intervals and the results obtained each time the method is performed may be compared. This information may be used to determine any changes in an individual subject's prognosis over the course of time.

The term "prognosis" is used herein to broadly encompass the prediction of any aspect of disease outcome for any given individual. In certain embodiments, the methods are used to predict disease severity in a patient. Alternatively or in addition, the methods may be used to assess the likelihood or risk of disease progression for any given patient and/or the likelihood or risk of worsening symptoms.

For patients having diseases or disorders characterised by increased RTK activation, the detection of one or more RTK oligomers may be linked to a poor prognosis. Alternatively or in addition, the detection of one or more oligomers having a different spatial separation of RTK molecules as compared with a control sample may be linked to a poor prognosis. As discussed above, the precise spatial separation of RTK molecules in an oligomer can be indicative of underlying mutations in RTK molecules and therefore information regarding the spatial separation of RTK molecules can serve as a prognostic biomarker.

A poor prognosis may manifest as an increased risk of disease progression or an increased risk of worsening symptoms. If an individual or patient is classified at "increased risk", this means that their risk of, for example, disease progression, is higher than the level of risk that would be associated with any given individual based on the standard course of disease progression measured across a larger or more significant patient population.

The results of the methods carried out to determine patient prognosis may be used to stratify patients. For example, it may be possible to use the results of the methods described herein to classify patients into "high-risk" and "low-risk" categories, and potentially subdivisions of such categories. Patients found to have one or more RTK oligomers, or a higher number of RTK oligomers per cell or cell sample, may be classified as high-risk whereas those found to have fewer RTK oligomers may be classified as low-risk. Alternatively or in addition, patients may be stratified according to the precise spatial separation of RTK molecules within oligomer complexes detected at the surface of cells. Such stratification of patients may be used to inform subsequent treatment decisions.

The methods of the present invention may be carried out to determine patient prognosis for a subject having any disease characterised by aberrant RTK activation. In certain embodiments, the disease will be selected from: cancer, diabetes, cardiovascular disease including atherosclerosis, inflammatory disorders, bone disorders, neurodegenerative diseases including Alzheimer's disease and motor neurone disease, and arthritis.

In preferred embodiments of the invention, the disease characterised by aberrant RTK activation is cancer, and the methods are carried out to determine patient prognosis for any given cancer patient. Cancer patients may be selected from those having any of the following types of cancer: non-small-cell lung cancer, small-cell lung cancer, breast cancer, prostate cancer, renal cell cancer, colorectal cancer, glioma, hepatic cancer, melanoma, pancreatic cancer, oesophageal cancer, ovarian cancer, cervical cancer, lymphoma and leukaemia, head and neck cancer, gastric cancer, endometrial cancer, bladder cancer, squamous and basal cell carcinoma, bone cancer metastasis.

RTK activation is frequently increased or elevated in cancer and therefore the detection of one or more RTK oligomers in a cell sample, particularly a tumour biopsy isolated from a cancer patient, may be indicative of a poor prognosis. Mutations in RTKs leading to aberrant RTK activation have also been associated with the onset and progression of cancer, and therefore the detection of one or more RTK oligomers having a particular spatial separation of RTK molecules, may be indicative of one or more underlying RTK mutations linked to poor prognosis.

In the context of cancer, a poor prognosis may manifest as increased tumour aggressiveness wherein aggressiveness is measured as the extent to which the tumour cells have invaded surrounding tissue. Alternatively or in addition, a poor prognosis may manifest as an increased likelihood of cancer metastasis i.e. the formation of tumours at secondary sites in the body.

In the methods of determining patient prognosis described herein, the RTK oligomers may be oligomers of any RTK molecules, particularly the human RTKs shown in Table 1 or mutant or variant forms thereof. For embodiments wherein the methods are carried out to determine cancer patient prognosis, the RTK molecules for imaging are preferably selected from the EGFR family of RTKs i.e. EGFR, ErbB2, ErbB3 and ErbB4, most preferably EGFR. As noted above, dysregulated signalling via members of the EGFR RTK family has been linked to the development and progression of a several cancer types. Therefore, the imaging of EGFR molecules at the cell surface of cancer cells and the detection of RTK oligomers may be an effective means to determine prognosis in patients having cancers wherein EGFR or EGFR family members are known to drive tumour progression. In certain embodiments, the methods of the present invention will be carried out to determine patient prognosis for a subject having a cancer selected from non-small-cell lung cancer, breast cancer and glioma or glioblastoma and the presence of one or more EGFR oligomers, particularly EGFR tetramers, will be indicative of poor patient prognosis.

Patients identified as having a poor prognosis may be selected for treatment. The methods as described herein may comprise an additional step of administering to a subject a therapeutic agent in an amount suitable for the treatment of the patient's disease or condition. For embodiments wherein the disease is cancer, a patient identified as having a poor prognosis may be treated with any suitable anti-cancer treatment including but not limited to chemotherapy and/or radiotherapy. In certain embodiments, the patient identified as having a poor prognosis is treated by administration of a tyrosine kinase inhibitor that targets the RTK found to be present in oligomeric form on the surface of the patient's cancer cells.

Selecting Patients for Treatment

As explained above, RTKs are attractive therapeutic targets because of their link with many different diseases, notably cancer. Many tyrosine kinase inhibitors have been developed and are currently being developed as therapeutic agents, particularly as anti-cancer agents. There are several difficulties associated with the development and use of targeted therapies such as tyrosine kinase inhibitors, including costs associated with the pre-clinical and clinical developmental stages, differential patient responses to treatment and the onset of resistance in certain patients. In order to improve the development and use of targeted medicines, it is often desirable to select patients for treatment by screening for biomarkers that correlate with patient responsiveness. The RTK oligomers for imaging and detection according to the methods described herein are particularly suitable for use in methods of screening subjects as part of a personalised approach to treatment, for the reason that these biomarkers provide a read-out of RTK activation in cells.

It follows that in a further aspect, the present invention provides a method of selecting a subject for treatment with a RTK inhibitor, wherein the method comprises the steps of imaging RTK molecules and detecting the presence and/or structure of RTK oligomers according to any of the embodiments described herein. The RTK molecules that are imaged are the target of the RTK inhibitor to be used in treatment. For example, if the method is directed to selecting a subject for treatment with an EGFR inhibitor, then the method will comprise steps of imaging EGFR molecules and detecting the presence and/or structure of one or more EGFR oligomers at the cell surface. If one or more RTK oligomers is/are detected at the cell surface, then the subject is selected for treatment. Alternatively or in addition, if one or more RTK oligomers having a spatial separation of RTK molecules indicative of aberrant RTK activation is/are detected at the cell surface, then the subject is selected for treatment. In this aspect of the invention, a sample taken from a subject or individual under test may be compared with a sample taken from a control or reference subject such that the results of the RTK imaging can be compared. The control or reference sample may have a normal level of RTK activation and/or signalling i.e. a level that is not associated with the development or progression of disease. In such embodiments, if the spatial separation of RTK molecules in oligomer complexes in the sample taken from the individual or subject under test is found to be different from the control or reference, then the subject is selected for treatment.

Many tyrosine kinase inhibitors are known in the art including RTK inhibitors developed as anti-cancer agents, for example those listed in Table 2 above. The present methods may be carried out to select a subject for treatment with any RTK inhibitor including but not limited to EGFR inhibitors, VEGFR inhibitors and PDGFR inhibitors.

In certain embodiments, the methods will be carried out in relation to a sample of cells isolated from a subject that has already been diagnosed with a disease or disorder characterised by aberrant RTK activation, particularly wherein the disease is cancer. In such embodiments, the method may be carried out to determine whether or not activation of a particular RTK, for example an RTK of the EGFR family, is dysregulated in the diseased cells of the patient and thereby determine whether the patient is suitable for treatment with an RTK inhibitor targeting that particular RTK.

In preferred embodiments, the present methods are carried out to select a cancer patient for treatment with an inhibitor of a RTK in the EGFR family, particularly an EGFR inhibitor. The EGFR inhibitor may be selected from: Gefitinib (Iressa), Erlotinib (Tarceva), Lapatinib, Canertinib, Cetuximab (Erbitux) and Panitumumab (Vectibix).

The methods as described herein directed to selecting subjects for treatment may be carried out in the context of monitoring patients as part of an ongoing treatment plan. For example, the subject from which a sample containing cells is isolated may have already received the RTK inhibitor of interest and the method may be carried out to determine whether it is appropriate to continue with treatment. Alternatively or in addition, the subject from which a sample containing cells is isolated may have already received the RTK inhibitor and may have developed apparent resistance to the inhibitor. The method may therefore be carried out to determine whether elevated RTK activation is still present in the diseased cells to thereby determine whether or not to continue with treatment. Alternatively or in addition, the method may be carried out to determine whether one or more mutations are present within the RTK in the diseased cells, wherein one or more mutations may be indicative of the acquisition of resistance. The methods may also be carried out to select subjects for enrolment in clinical trials designed to test one or more new RTK inhibitors.

The methods as described herein may additionally comprise a step of administering to a subject selected for treatment the RTK inhibitor of interest. The RTK inhibitor may be administered according to any route or dosage regimen deemed to be appropriate by a person skilled in the art, typically a medical professional.

The invention will now be further understood with reference to the following non-limiting examples.

EXAMPLES

Example 1 Detection of EGFR Oligomers Using FLImP Imaging

A) Sample Preparation

Chinese Hamster Ovary (CHO) cells were cultured in Dulbecco's Modified Eagle Medium (DMEM) without phenol red and supplemented with 10% Foetal Calf Serum (FCS), 2 mM L-Glutamine, 1% penicillin/streptomycin and 2 ml/l Geneticin (all Invitrogen). Cells were grown in 35 mm no. 1.5 high tolerance glass-bottomed dishes (MatTek Corporation, USA), treated with 1% Bovine Serum Albumin. Anti-EGFR affibody (Abcam) was labelled with CF640R maleimide (Biotium) and labelled affibody was separated from free dye using gel filtration chromatography (NAP-5 column, GE Healthcare), according to the manufacturer's instructions. The EGFR affibody was labelled at a 1:1 ratio at its single cysteine residue. Cells were rinsed with PBS and cooled to 4° C. for 10 min. Cells were labelled with 0.5 nM EGFR Affibody-Atto CF640R for 30 min at 4° C. Cells were rinsed with PBS and fixed with 3% paraformaldehyde plus 0.5% glutaraldehyde for 15 min at 4° C. then 15 min at room temperature. Cells were fixed to avoid fluorophore movements relative to the cells during image collection, and were then placed in a suitable total internal reflection fluorescence (TIRF) for single molecule imaging.

B) Single Molecule Microscopy

Key requirements for single molecule TIRF imaging are a high magnification, high numerical aperture (>1.4) objective lens, and an electron multiplying CCD detector. An Axiovert 200M microscope with TIRF illuminator (Zeiss, UK), incorporating a 100× oil-immersion objective (α-Plan-Fluar, NA=1.45; Zeiss, UK), and an iXon X3 EMCCD (Andor, UK) was used for the experiments described herein. Standard diode lasers can be used for illumination, provided that they have sufficient power to deliver intensities of 0.5 $\mu W/\mu m2$ at the sample. Red lasers are preferable as they excite less background fluorescence than shorter wavelengths. In the system used herein, illumination was provided by a fibre-coupled laser combiner (Andor) incorporating a 100 mW 640 nm diode laser (Cube, Coherent). A major factor affecting resolution of FLImP is sample drift and instability. For this reason it was essential that the microscope was located on a vibration-isolating optical table, and that the laboratory temperature was highly stable (±0.5° C. or better). The microscope stage was also isolated as much as possible from the laboratory environment, in particular from air currents, and this was achieved by enclosing it in a chamber, in particular an XL-3 multi S incubator (Pecon, Germany), which is specifically designed for the Axiovert 200M.

Stability of the sample, the microscope, and the general laboratory environment is critical for successful high resolution FLImP measurements. All equipment was switched on at least 30 minutes before experiments began, and samples were left on the microscope sample stage for at least 20 minutes after a suitable area had been identified before collecting data. Movement and noise within the laboratory was kept to a minimum during data collection. The first step was to select a suitable area of the sample for imaging. Suitable areas were selected as those with a reasonable density of fluorescent spots, but not so dense that there was a significant level of overlap between spots. Areas with patches of diffuse fluorescence were avoided. It was also necessary to check the white light image to ensure that cells were present; in some cases fluorescent features may be seen in the absence of cells, due to is non-specific binding to the coverslip. Suitable areas were found and focussed using a low laser power (~0.2 mW), enough to be able to distinguish the spots and without bleaching the sample. After a suitable area was found it was necessary to wait for 2 minutes to ensure that the stage had stabilised. The laser power was then increased to the level required for data acquisition (4 mW for CF640R), the microscope refocused if needed, and data acquisition started within around 5 seconds to avoid significant photobleaching before data collection began. Single molecule data were collected every 280 ms until most of the fluorescent spots had photobleached.

C) Data Analysis

Data analysis was carried out using custom-designed software, as published (Needham et al. Measuring EGFR separations on cells with ~10 nm resolution via fluorophore localization imaging with photobleaching. PLoS One. 2013 May 1; 8(5): e62331; Rolfe et al., Automated multidimensional single molecule fluorescence microscopy feature detection and tracking. European Biophysics Journal, 2011 40: 1167-86). Spots were identified and their intensities tracked versus time using custom Bayesian algorithms. Tracks were formed by linking detected features between frames, with gaps due to blinking filled by interpolating linearly in position. Spots potentially suitable for FLImP analysis were identified by three characteristics: Two constant intensity levels separated by a photobleaching step (levels 1 and 2, respectively); the lowest level decays to zero intensity after photobleaching; and each level contains more than 5 frames of data (1.4 s). A model of two fluorophores was then fitted to each spot, assuming a Gaussian profile for each fluorophore. A global least-squares 7-parameter fit was used to identify intensity, x and y positions, and PSF FWHM for each fluorophore. The probability distribution of the model parameters was assessed using the Monte Carlo bootstrap method, and the x and y fluorophore positions converted to a distribution of separations, giving a best fit value and an associated 68% confidence interval (CI) that contains 68% of the bootstrap separation values nearest to the best fit value. Combining the data from a number of spots gave a CI-plot that shows the range of distances between the fluorophores that have been measured. The software also corrected for sample drifts, which in our experience range from around 0.03 to 2 nm/s. The global sample drift was determined by superimposing all the tracks from an image and performing a least-squares fit of a quadratic model to their mean track.

The FLImP model assumes homogeneous background, two fluorophores with constant intensity, and Gaussian noise. Fluorophore blinking is not included in the model, nor are any other artefacts. Therefore, selection of appropriate spots, and selection of appropriate areas for analysis within the tracks from those spots was key to achieving the best resolution. The algorithm was able to perform some pre-selection of traces, and characteristics taken into account for the tracks are as follows:

1. The agreement of the levels intensity trace with the level model (using a $\chi^2$ statistic).
2. The number of non-zero intensity levels in the trace (at least two).
3. The number of detected spots in each level.
4. The trace bleaches completely during acquisition.
5. The proportion of the features in a trace that are detected rather than interpolated.
6. The minimum distance to closest neighbour, usually about 5 pixels (=800 nm).
7. The distance of the mean position of features in level 1 and features in level 2; the distance is roughly half the expected separation of the fluorophores.
8. The total spread of the fluorophore positions.
9. The number of spots in a trace that are assigned to a constant intensity level.
10. The standard error in mean of the distance of the mean positions in level 1 and level 2.
11. The signal to noise ratio of the feature intensity in level 1 and level 2; note that the SNR is expected to be higher in level 2 than in level 1.
12. The background homogeneity.
13. The length of level 1 and level 2.
14. The constancy of the intensity in level 1 and level 2.
15. The size of the intensity steps.

Scores were derived to assess these characteristics for each trace. Although filters based on these scores remove spots that are clearly unsuitable for analysis, further filtering by eye was required, to eliminate problems such as spots in close proximity to each other, uneven backgrounds, and unstable sample drift. A "good" trace fulfilled the requirements for the FLImP analysis in terms of its agreement with the model and yielded a low error in the estimate of the fluorophore separation. Once good traces had been selected, the regions corresponding to levels 1 and 2 were selected, and the traces submitted for analysis. Typically, a high resolution analysis requires data from around 50-70 traces.

The analysis was visualised in a confidence interval plot, referred to as the CI-Plot. This plot shows the number of results consistent with the measurement of a particular distance, and can be considered as a set of Gaussians, each corresponding to a fluorophore separation measured in the sample. The upper panel of FIG. 1 shows a typical CI-plot, for wild-type EGFR labelled with affibody conjugated with CF640R dye. This plot shows the presence of multiple separations in the range from 10 to 70 nm, showing the presence of oligomers in inactive EGFR. Currently, fluorophore spacings are extracted from the CI-plots by Gaussian fitting, for which software is widely available. For the experiments described herein, Igor Pro (Wavemetrics) was used, which uses the Levenberg-Marquardt algorithm to search for the minimum value of chi square. The fitted Gaussians are shown in the lower panel of FIG. 1.

Example 2 EGFR Oligomers Form at Physiological EGF Concentrations

The formation of EGFR oligomers was detected using the same protocol as described above in Example 1. However instead of Affibody-CF640R, Epidermal Growth Factor (EGF) conjugated with the fluorescent dye CF640R and used at a concentration of 4 nM was used to label the cells. The addition of EGF results in activation of the receptors.

Cells were fixed with paraformaldehyde/glutaraldehyde and spacings between EGFR molecules measured using FLImP as described above. Analysis showed short spacings corresponding to inactive complexes (3.6 and 7.9 nm), active dimers (18.6 nm), hexamers (27.4 nm) and higher order oligomers.

Example 3 EGFR Separation is Affected by EGFR Mutations

The formation of EGFR oligomers was detected using the same protocol as described above in Example 1. However, FLImP measurements were also made on CHO cells expressing a number of EGFR mutants as described below. All cells were labelled with 4 nM EGF-CF640R.

CC (R647C/V650C): A double mutant in the inner juxtamembrane domain that becomes palmitoylated in the two cysteine residues. This mutant does not show high affinity EGF binding and its phosphorylation is defective.

Delta C: a mutant containing the extracellular and transmembrane domains of the EGFR but lacking the entire intracellular domain.

C'973: a mutant containing the extracellular and transmembrane domains of the EGFR, and also the inner juxtramembrane domain, the kinase domain and the adjacent first 19 residues of the C-terminus. The kinase domains can activate but it cannot become phosphorylated because it lacks the part of the C-terminus containing all tyrosine residues.

K618V: Mutation at the base of the extracellular domain that results in a constitutively active receptor.

K721A: Mutation in the kinase domain that completely abrogates the catalytic activity of the receptor.

Figure 3:
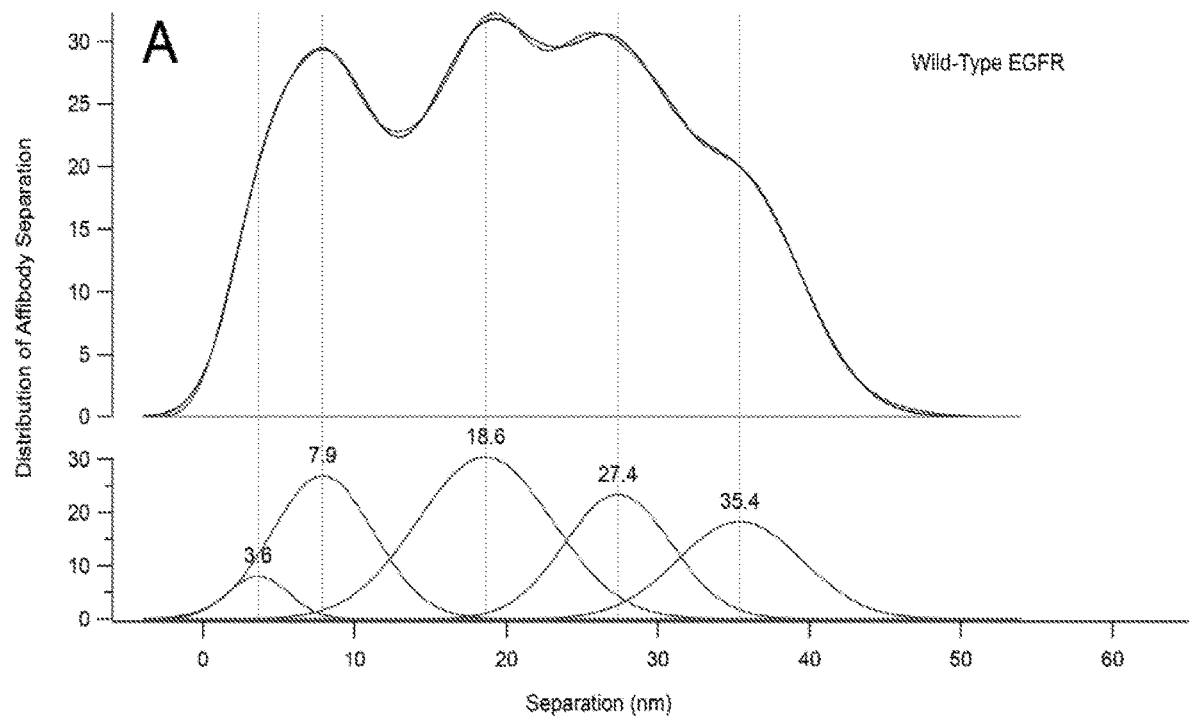
FIG. 3 FLImP data for separations between EGFR in CHO cells. Cells were labelled with 4 nM EGF conjugated with CF640R, and fixed with paraformaldehyde/glutaraldehyde before making the FLImP measurements. A shows separations for wild-type EGFR, B-F show separations for a number of EGFR mutants.
Figure 3:
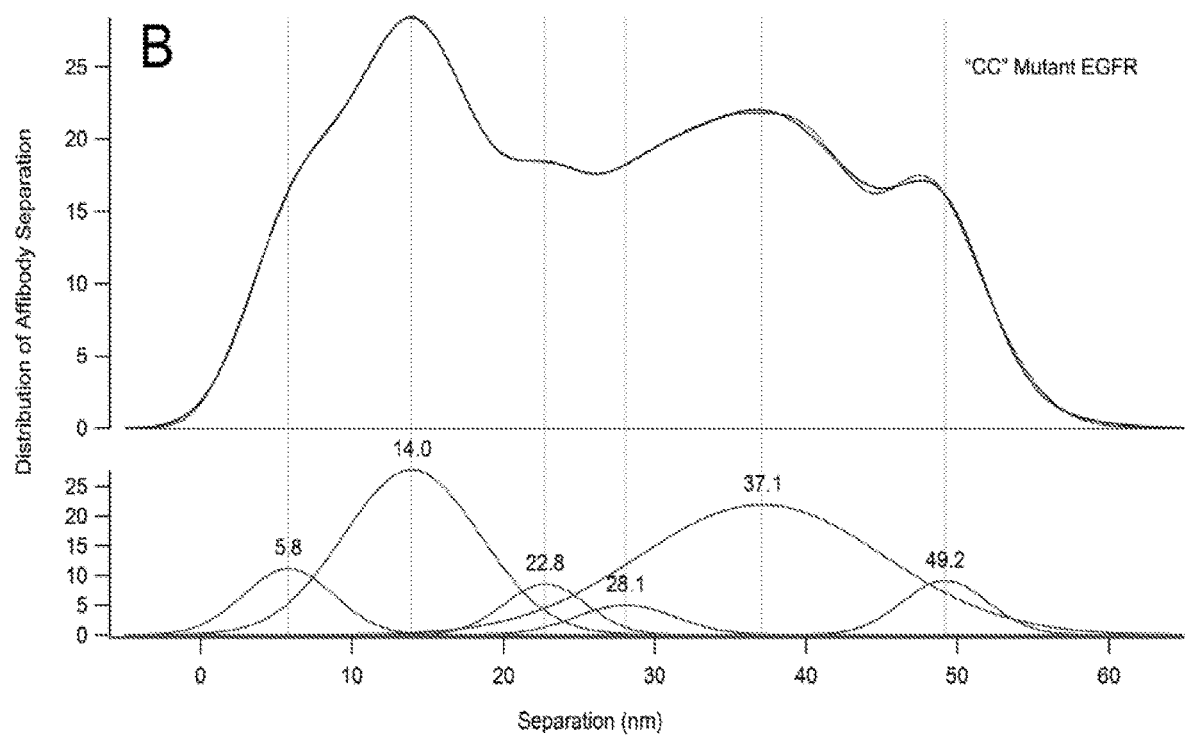
Figure 3:
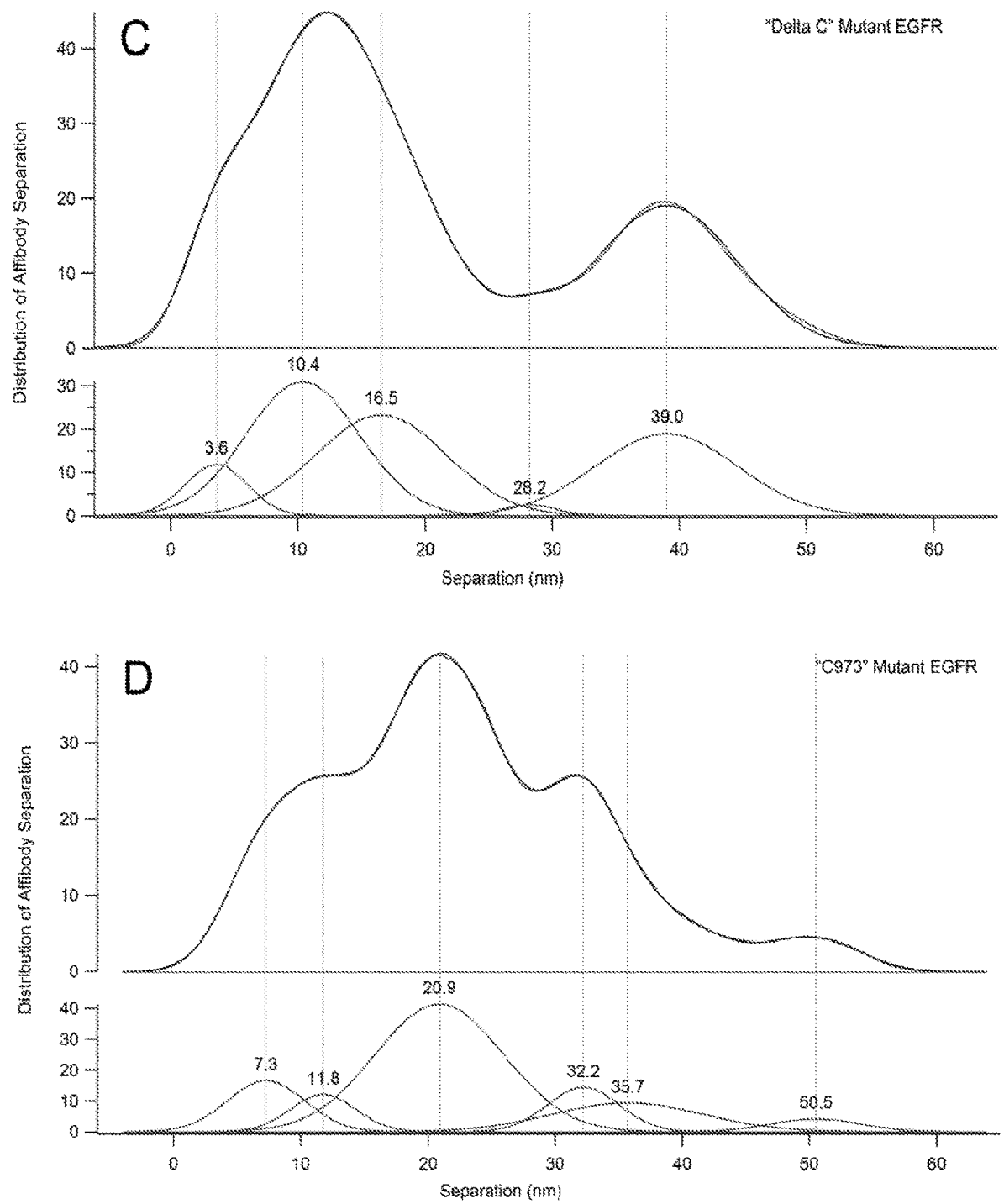
Figure 3:
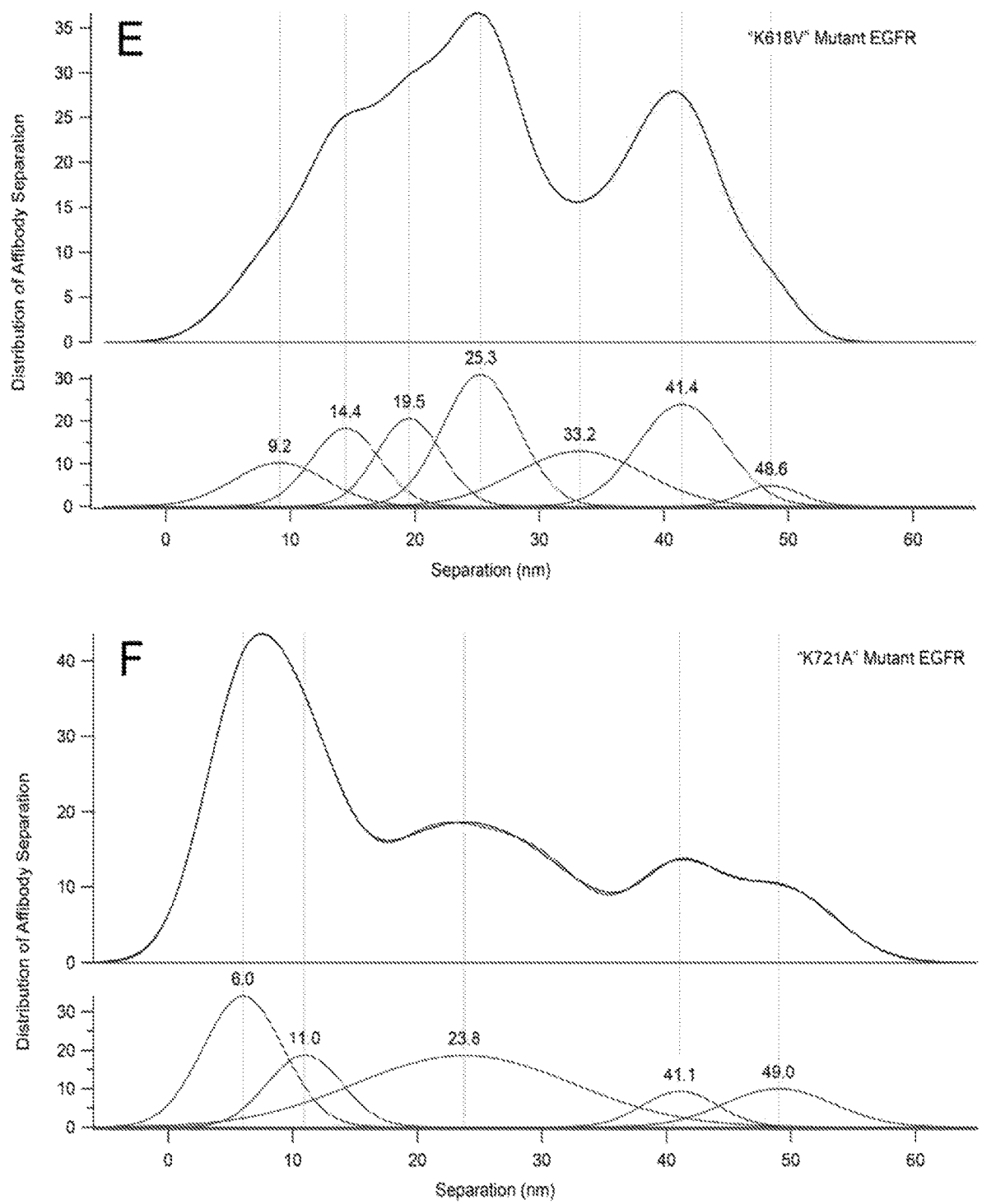

The results are shown in FIG. 3 and the data show that the pattern of separations is different for wild-type EGFR than for the mutants, and that the separation pattern also varies depending on the specific mutation.

Example 4 EGFR Oligomerisation is Critical for Optimal Autophosphorylation

CHO cells stably expressing WT-EGFR were seeded on 6-well plates at a density of 105 cells/well, grown to 80% confluency and serum-starved for 2 h. For the EGF dose-response curve, cells were treated with the indicated concentrations of unlabelled EGF (between 1 nM and 10 μM) for 2 h on ice. For a negative control, cells were treated with PBS. After washing off excess label, samples were treated with 1 mg/ml BS3 crosslinker (Sigma) in PBS for 30 min at 4° C. to cross-link proteins. The reaction wasquenched with 20 mM Tris pH 7.5 for 15 min on ice and then samples were washed twice with ice-cold PBS. Dishes were lysed for 5 min on ice with 400 μl hot lysis buffer (2×LDS buffer (Invitrogen) supplemented with 25 mM benzamidine, 1/100 Protease Inhibitor cocktail (Sigma) and 100 mM NaF, 1 mM $Na_3VO_4$ and 1% DTT. Lysates were cleared by centrifuging at 14000 g for 5 min at 4° C. Samples were run in parallel on 1.5 mm thick 3-8% Tris-Acetate NuPAGE gels (Invitrogen) with HiMark Prestained HMW and Novex Sharp Prestained protein standards (Invitrogen) using XCell apparatus (Invitrogen). Proteins were blotted using an iBlot system (Invitrogen) on PVDF membranes, blocked for 1 h at room temperature with 5% BSA in TBS+0.1% Tween and probed overnight with mouse anti-phosphotyrosine 4G10 or rabbit anti-EGFR pY1173 (both Upstate (Millipore)). Gels were probed with secondary anti-mouse or anti-rabbit-HRP antibody (Jackson ImmunoResearch) and incubated with Supersignal West Pico Chemiluminescent Substrate solution (Pierce) for 5 min, then imaged with a BioRadChemiDoc MP system imager. Each blot was stripped with 25 ml stripping buffer (2% SDS, 62.5 mM Tris HCl pH 6.7) with 187.5 μl β-mercaptoethanol for 50 min at 60° C., and re-probed with rabbit-anti total EGFR (Cell Signaling Technology). Anti-rabbit HRP (Jackson ImmunoResearch) was used for both blots and images were acquired as above.

Densitometry analysis was performed with ImageJ software (NIH). Bands were normalized against the amount of total EGFR and relative quantity was expressed as fold change compared to the negative control. Results are plotted in FIG. 4A. As EGF concentration increases, phosphorylation decreases.

Figure 4:
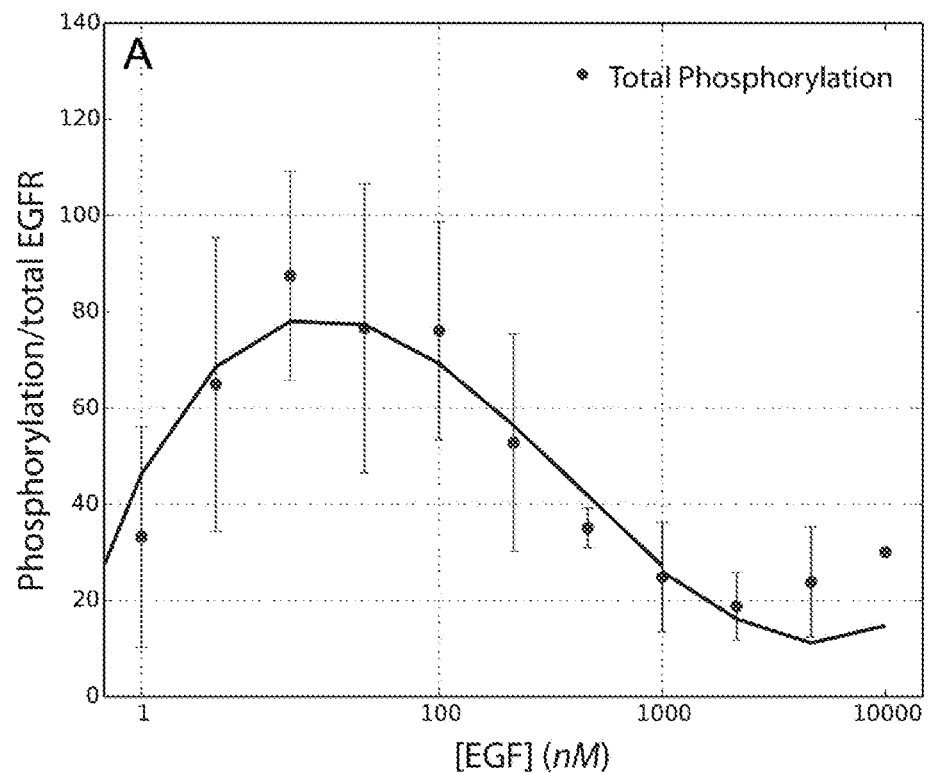
FIG. 4 Phosphorylation of EGFR was measured by Western blotting (A). Phosphorylation is at a maximum with physiological concentrations of EGF (~4 nM), and decreases as EGF concentration goes above 100 nM. (B) Plot derived from FLImP data showing variation of separation of EGFR between 12 and 20 nm, with varying EGF concentration. A separation of around 18 nm is consistent with the presence of tetramers and higher-order oligomers, while separations between 13 and 15 nm indicate the presence of dimers. Correlation between phosphorylation and the specific pattern of oligomer formation is shown in panels C and D. Panel (C) shows the FLImP measurement of EGFR-EGFR separation at physiological EGF concentration (4 nM). This shows a characteristic peak at around 18 nm, corresponding to active oligomers. As EGF concentration increases, for example at 400 nM (D) the 18 nm peak shifts to shorter distances. This is consistent with a loss of higher order oligomers and parallels the reduction in phosphorylation shown in (A).
Figure 4:
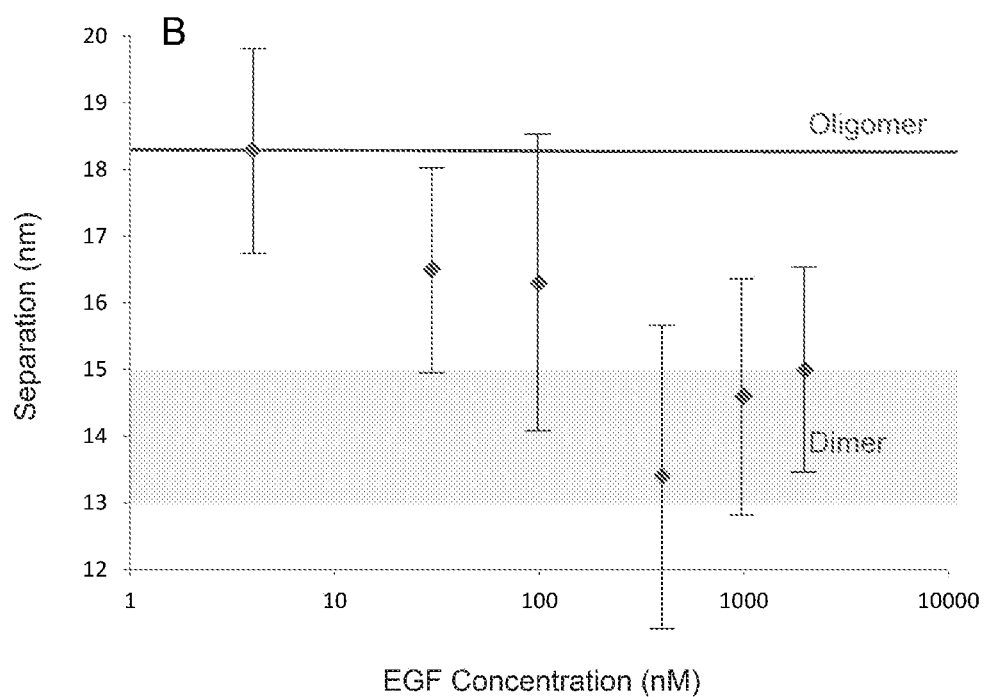
Figure 4:
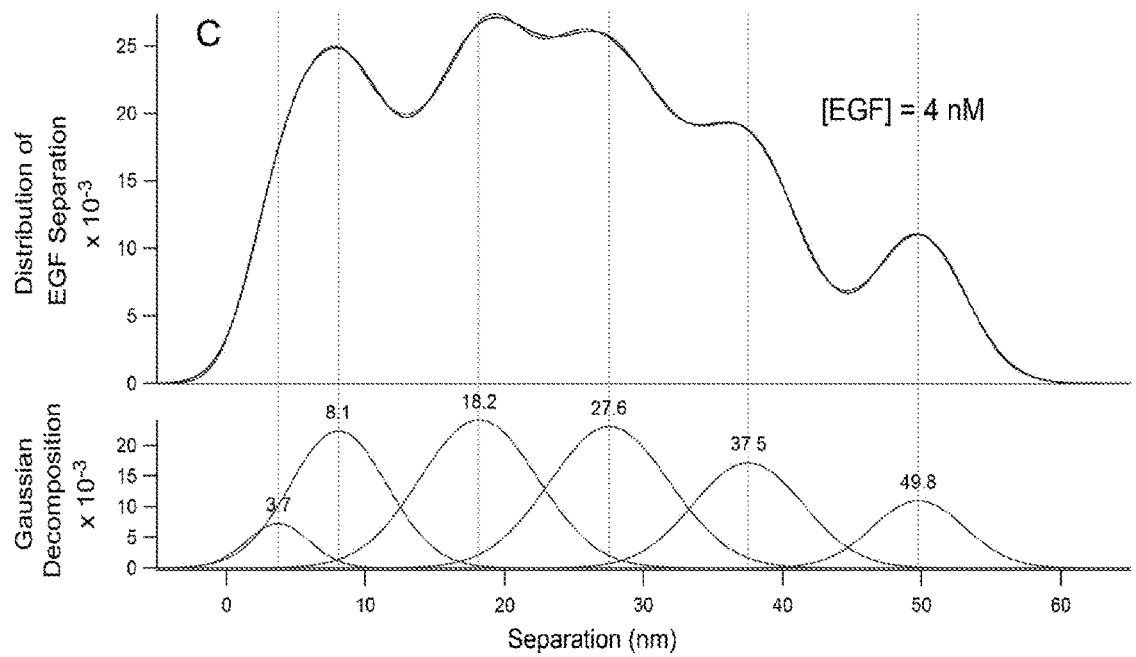
Figure 4:
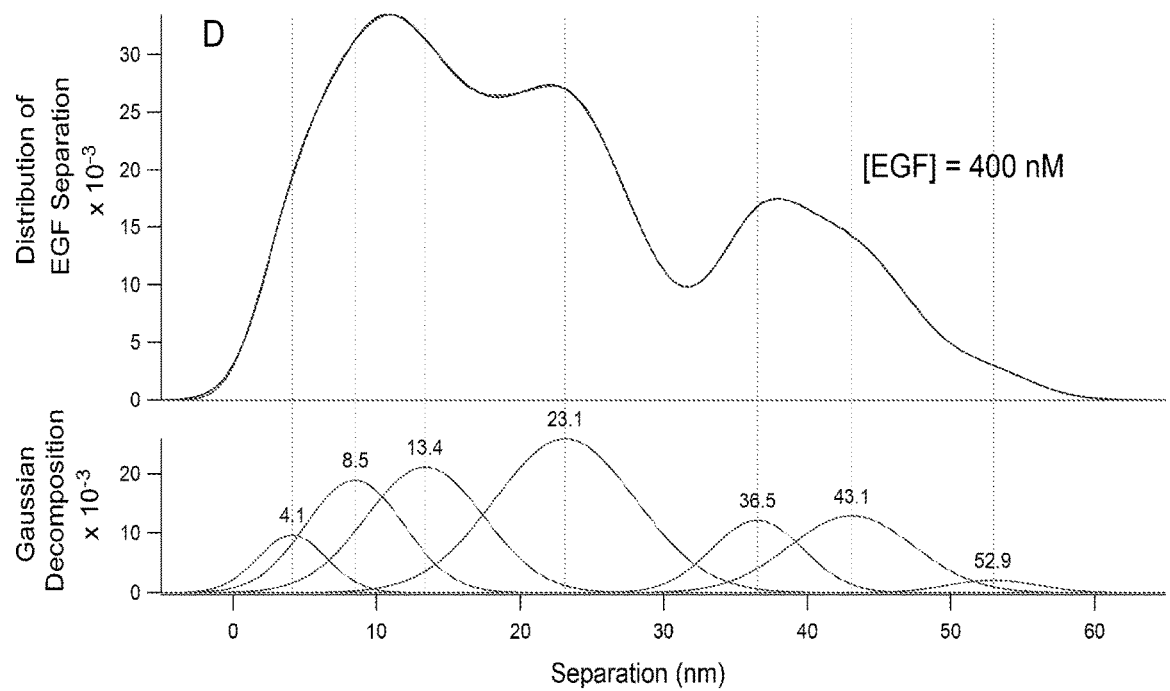

CHO cells treated with varying concentrations of EGF (4 nM, 400 nM, 1000 nM, and 2000 nM) were also anlysed by FLImP as described in Example 2 above. The results of this analysis are shown in FIG. 4B-D. FIG. 4B shows the change in position of the EGFR separation located between 12 and 20 nM. At physiological EGF concentrations, this separation is measured at 18.2 nm, a distance consistent with the presence of oligomers (e.g. tetramers). At higher EGF concentrations, the peak shifts to around 14 nm, consistent with the loss of higher order oligomers. The shift in position follows the level of phosphorylation shown in FIG. 4A, showing that oligomerisation is required for optimal phosphorylation of the receptor. Example FLImP measurements are shown in FIGS. 4C and D. At physiological EGF concentration (4 nM) the receptor is fully phosphorylated and the separation is 18.2 nm. At high EGF concentration (400 nM), phosphorylation is reduced and the peak is shifted to 13.4 nm.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate.

Various publications and patent applications are cited herein, the disclosures of which are incorporated by reference in their entireties.

The invention claimed is:

1. A method of treating a subject comprising
   (i) obtaining a sample of cells from a subject,
   (ii) detecting the presence of one or more receptor tyrosine kinase (RTK) oligomers in one or more cells in the sample by contacting the one or more cells with a fluorophore-conjugated RTK ligand or a fluorophore-conjugated RTK-specific affibody, and detecting binding between RTK monomers and the fluorophore-conjugated RTK ligand or the fluorophore-conjugated RTK-specific affibody, wherein RTK is EGFR/ErbB1, ErbB2, ErbB3 or ErbB4, and wherein each RTK oligomer comprises more than two RTK monomers,
   (iii) determining the nanometre spatial separation between RTK monomers assembled in any of the one or more RTK oligomers,
   (iv) identifying the subject as having the nanometre spatial separation between RTK monomers assembled in the one or more RTK oligomers, and
   (v) administering to the subject an effective amount of an RTK inhibitor selected from Gefitinib (Iressa), Erlotinib (Tarceva), Lapatinib, Canertinib, Cetuximab (Erbitux) and Panitumumab (Vectibix).

2. The method of claim 1 wherein the subject has been diagnosed with a disease, and wherein the disease is selected from diabetes, cardiovascular disease including atherosclerosis, inflammatory disorders, bone disorders, neurodegenerative diseases including Alzheimer's disease and motor neurone disease, and arthritis.

3. The method of claim 1 wherein the subject has been diagnosed with a cancer selected from non small-cell lung cancer, small-cell lung cancer, breast cancer, prostate cancer, renal cell cancer, colorectal cancer, glioma, hepatic cancer, melanoma, pancreatic cancer, oesophageal cancer, prostate cancer, ovarian cancer, cervical cancer, lymphoma, leukaemia, head and neck cancer, gastric cancer, endometrial cancer, bladder cancer, squamous and basal cell carcinoma, and bone cancer metastasis.

4. The method of claim 1 wherein the binding between the RTK monomers and the fluorophore-conjugated RTK ligand or the fluorophore-conjugated RTK-specific affibody is detected using a high-resolution imaging method.

5. The method of claim 1 wherein the RTK oligomers are
   (a) selected from hexamers, or higher-order oligomers consisting of at least 8, at least 10, at least 12, at least 14, at least 16, at least 18, at least 20 RTK monomers, or
   (b) tetramers.

6. The method of claim 1 wherein the binding between the RTK monomers and the fluorophore-conjugated RTK ligand or the fluorophore-conjugated RTK-specific affibody is detected using Fluorophore Localisation Imaging with Photobleaching (FLImP).

7. A method of treating a subject comprising administering an effective amount of a receptor tyrosine kinase (RTK) inhibitor to a subject having RTK activation as determined by
   (i) obtaining a sample of cells from a subject; and
   (ii) detecting the presence of one or more RTK oligomers in one or more cells in the sample by contacting the one or more cells with a fluorophore-conjugated RTK ligand or a fluorophore-conjugated RTK-specific affibody, and detecting binding between RTK monomers and the fluorophore-conjugated RTK ligand or the fluorophore-conjugated RTK-specific affibody,
   wherein each RTK oligomer comprises more than two RTK monomers,
   wherein the presence of one or more RTK oligomers is indicative of RTK activation in the one or more cells,
   wherein RTK is EGFR/ErbB1, ErbB2, ErbB3 or ErbB4, and
   wherein the RTK inhibitor is selected from Gefitinib (Iressa), Erlotinib (Tarceva), Lapatinib, Canertinib, Cetuximab (Erbitux) and Panitumumab (Vectibix).

8. The method of claim 7 wherein the subject has a cancer.

9. The method of claim 1 wherein the one or more cells are contacted with a fluorophore-conjugated RTK ligand, and binding between RTK monomers and the fluorophore-conjugated RTK ligand is detected.

10. The method of claim 9 wherein the RTK is EGFR.

11. The method of claim 9 wherein the binding between RTK monomers and the fluorophore-conjugated RTK ligand is detected using Fluorophore Localisation Imaging with Photobleaching (FLImP).

12. The method of claim 1 wherein the one or more cells are contacted with a fluorophore-conjugated RT-specific affibody, and binding between RTK monomers and the fluorophore-conjugated RTK-specific affibody is detected.

13. The method of claim 12 wherein the RTK is EGFR.

14. The method of claim 12 wherein the binding between RTK monomers and the fluorophore-conjugated RTK-specific affibody is detected using Fluorophore Localisation Imaging with Photobleaching (FLImP).

15. The method of claim 1 wherein the RTK inhibitor is Erlotinib (Tarceva).

16. The method of claim 7 wherein the RTK inhibitor is Erlotinib (Tarceva).

17. The method of claim 1 wherein the RTK oligomers are tetramers.

18. The method of claim 7 wherein the RTK oligomers are tetramers.

* * * * *